(12) United States Patent
Shin et al.

(10) Patent No.: US 11,713,326 B2
(45) Date of Patent: Aug. 1, 2023

(54) COMPOUND AND PHOTOELECTRIC DEVICE, IMAGE SENSOR AND ELECTRONIC DEVICE INCLUDING THE SAME

(71) Applicant: Samsung Electronics Co., Ltd., Suwon-si (KR)

(72) Inventors: Jisoo Shin, Seoul (KR); Chul Baik, Suwon-si (KR); Sung Young Yun, Suwon-si (KR); Taejin Choi, Suwon-si (KR); Kyung Bae Park, Hwaseong-si (KR); Gae Hwang Lee, Seongnam-si (KR); Yeong Suk Choi, Suwon-si (KR); Chul Joon Heo, Busan (KR); Hye Rim Hong, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 427 days.

(21) Appl. No.: 16/938,031

(22) Filed: Jul. 24, 2020

(65) Prior Publication Data

US 2021/0024544 A1 Jan. 28, 2021

(30) Foreign Application Priority Data

Jul. 26, 2019 (KR) .................. 10-2019-0091284

(51) Int. Cl.
*C07D 517/04* (2006.01)
*H10K 85/60* (2023.01)
*H10K 30/30* (2023.01)

(52) U.S. Cl.
CPC ......... *C07D 517/04* (2013.01); *H10K 85/621* (2023.02); *H10K 85/657* (2023.02); *H10K 30/30* (2023.02)

(58) Field of Classification Search
CPC ...... H01L 31/00–078; Y02E 10/50–60; H10K 30/00–89
(Continued)

(56) References Cited

U.S. PATENT DOCUMENTS 5,783,575 A 7/1998 Jakobsen et al.
6,300,612 B1 10/2001 Yu
7,129,466 B2 10/2006 Iwasaki
(Continued)

FOREIGN PATENT DOCUMENTS

CN 107235990 A 10/2017
EP 3442022 A1 2/2019
(Continued)

OTHER PUBLICATIONS

Extended European Search Report dated Nov. 16, 2020, issued in corresponding European Application No. 20187701.6.
(Continued)

*Primary Examiner* — Bach T Dinh
(74) *Attorney, Agent, or Firm* — Harness, Dickey & Pierce, P.L.C.

(57) ABSTRACT

A compound of Chemical Formula 1, and an organic photoelectric device, an image sensor, and an electronic device including the same are disclosed:

[Chemical Formula 1]

(Continued)

In Chemical Formula 1, each substituent is the same as defined in the detailed description.

19 Claims, 9 Drawing Sheets

(58) Field of Classification Search
USPC .................................................. 136/243–265
See application file for complete search history.

(56) References Cited

U.S. PATENT DOCUMENTS

| | | | |
|---|---|---|---|
| 7,973,307 | B2 | 7/2011 | Rand et al. |
| 8,035,708 | B2 | 10/2011 | Takizawa et al. |
| 8,426,727 | B2 | 4/2013 | Pfeiffer et al. |
| 8,525,577 | B2 | 9/2013 | Yofu et al. |
| 9,666,810 | B2 | 5/2017 | Yun et al. |
| 9,786,847 | B2 | 10/2017 | Lim et al. |
| 9,818,956 | B2 | 11/2017 | Ro et al. |
| 9,941,477 | B2 | 4/2018 | Choi et al. |
| 10,096,781 | B2 | 10/2018 | Tadao et al. |
| 10,224,486 | B2 | 3/2019 | Yagi et al. |
| 10,276,802 | B2 | 4/2019 | Shibuya et al. |
| 10,326,083 | B2 | 6/2019 | Yagi et al. |
| 10,461,256 | B2 | 10/2019 | Choi et al. |
| 2007/0012955 | A1 | 1/2007 | Ihama |
| 2012/0313088 | A1 | 12/2012 | Yofu et al. |
| 2016/0211465 | A1 | 7/2016 | Tadao et al. |
| 2017/0092868 | A1 | 3/2017 | Yagi et al. |
| 2017/0346016 | A1* | 11/2017 | Bulliard .............. H01L 51/0068 |
| 2017/0352811 | A1 | 12/2017 | Choi et al. |
| 2020/0194679 | A1* | 6/2020 | Fukuzaki ............. C07D 307/66 |

FOREIGN PATENT DOCUMENTS

| | | | |
|---|---|---|---|
| JP | 201231143 | A | 2/2012 |
| JP | 2018002690 | A | 1/2018 |
| JP | WO2019049946 | * | 3/2019 |
| KR | 20160089809 | A | 7/2016 |

OTHER PUBLICATIONS

Guilherme M. Martins et al., 'SeCi2-Mediated Approach Toward Indole-Containing Polysubstituted Selenophenes' *The Journal or Organic Chemistry*, vol. 83, 2018, pp. 3252-3264.

François Baert et al., 'Theino[2,3-b]indole-Based Small Push-Pull Chromophores: Synthesis, Structure, and Electronic Properties' *Organic Letters*, Feb. 2016.

Penghui Ni et al., 'Solvent-controlled highly regio-selective thieno[2,3-b]indole formation under metal-free conditions' *Green Chemistry*, 2017.

Bin Li et al., 'Three-Component Thieno[2,3-b]indole Synthesis from Indoles, Alkenes or Alkynes and Sulfur Powder under Metal-Free Conditions' *Advanced Synthesis and Catalysis*, 2017.

Iryna Savych et al., 'Synthesis of Functionalized 2-Salicyloylfurans, Furo[3,2-b]chromen-9-ones and 2-Benzoyl-8H-thieno[2,3-b]indoles by One-Pot Cyclizations of 3-Halochromones with-βKetoamides and 1,3-Dihydroindole-2-thiones' *Organic & Biomolecular Chemistry*, Oct. 2014.

Mikio Ihama et al., 'CMOS Image Sensor with a Thin Overlaid Panchromatic Organic Photoconductive Layer for Sensors with Reduced Pixel Size' INP 1-4, IDW 2009, pp. 2123-2126.

Satoshi Aihara et al., 'Stacked Image Sensor With Green- and Red-Sensitive Organic Photoconductive Films Applying Zinc Oxide Thin-Film Transistors to a Signal Readout Circuit' *IEEE Transactions on Electron Devices*, vol. 56, No. 11, Nov. 2009, pp. 2570-2576.

Hokuto Seo et al., 'Color Sensors with Three Vertically Stacked Organic Photodetectors' *Japanese Journal of Applied Physics*, vol. 46, No. 49, 2007, pp. L1240-L1242.

Seon-Jeong Lim et al., 'Organic-on-silicon complementary metal-oxide-semiconductor colour image sensors' Scientific Reports, 5:7708, Jan. 2015.

Juha Alakarhu, 'Image Sensors and Image Quality in Mobile Phones' *International Image Sensor Workshop*, Jun. 2007.

* cited by examiner

COMPOUND AND PHOTOELECTRIC DEVICE, IMAGE SENSOR AND ELECTRONIC DEVICE INCLUDING THE SAME

CROSS-REFERENCE TO RELATED APPLICATION

This application claims priority to and the benefit of Korean Patent Application No. 10-2019-0091284 filed in the Korean Intellectual Property Office on Jul. 26, 2019, the entire contents of which are incorporated herein by reference.

BACKGROUND

1. Field

Example embodiments provide a compound and a photoelectric device, an image sensor, and an electronic device including the same.

2. Description of the Related Art

A photoelectric device converts light into an electrical signal using photoelectric effects. The photoelectric device may include a photodiode, a phototransistor, and the like, and it may be applied to an image sensor, an organic light emitting diode, and the like.

An image sensor including a photodiode requires high resolution and thus a small pixel. At present, a silicon photodiode is widely used, but it has a problem of deteriorated sensitivity since silicon photodiode has a smaller absorption area due to small pixels. Accordingly, an organic material that is capable of replacing silicon has been researched.

The organic material may have a high extinction coefficient and may selectively absorb light in a particular wavelength region depending on a molecular structure, and thus may simultaneously replace a photodiode and a color filter and resultantly improve sensitivity and contribute to high integration.

SUMMARY

Example embodiments provide a compound capable of selectively absorbing light in a green wavelength region and having improved thermal stability.

Example embodiments also provide a photoelectric device (e.g., organic photoelectric device) capable of selectively absorbing light in the green wavelength region and maintaining good efficiency even under high temperature conditions.

Example embodiments also provide an image sensor including the photoelectric device (e.g., organic photoelectric device).

Example embodiments also provide an electronic device including the image sensor.

According to example embodiments, a compound is represented by Chemical Formula 1.

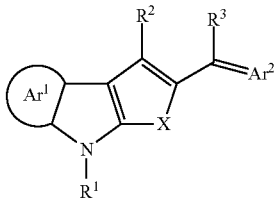

[Chemical Formula 1]

In Chemical Formula 1, $Ar^1$ is a substituted or unsubstituted C6 to C30 arene group or a substituted or unsubstituted C3 to C30 heteroarene group, $Ar^2$ is a substituted or unsubstituted C6 to C30 hydrocarbon cyclic group, a substituted or unsubstituted C6 to C30 heterocyclic group, or a fused ring thereof, $Ar^2$ has at least one functional group selected from C=O, C=S, C=Se, and C=Te, X is O, Se, Te, $SiR^aR^b$, or $GeR^cR^d$ (wherein $R^a$, $R^b$, $R^c$, and $R^d$ are independently hydrogen, deuterium, or a substituted or unsubstituted C1 to C10 alkyl group, and wherein $R^a$, $R^b$, $R^c$, and $R^d$ are independently present or $R^a$ and $R^b$ or $R^c$ and $R^d$ are linked with each other to provide a spiro structure), and $R^1$ to $R^3$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —$SiR^aR^bR^c$ (wherein $R^a$, $R^b$, and $R^c$ are independently hydrogen or a substituted or unsubstituted C1 to C10 alkyl group), or a combination thereof.

In some embodiments, in Chemical Formula 1, $R^1$ may be a substituted or unsubstituted C1 to C30 alkyl group or a substituted or unsubstituted C6 to C30 aryl group.

In some embodiments, in Chemical Formula 1, $Ar^1$ may be a substituted or unsubstituted benzene, a substituted or unsubstituted naphthalene, a substituted or unsubstituted indene, a substituted or unsubstituted anthracene, a substituted or unsubstituted phenanthrene, a substituted or unsubstituted fluorine, or a substituted or unsubstituted acenaphthylene.

In some embodiments, in Chemical Formula 1, $Ar^1$ may be a substituted or unsubstituted pyridine, a substituted or unsubstituted pyrimidine, a substituted or unsubstituted pyrazine, a substituted or unsubstituted indole, a substituted or unsubstituted quinoline, a substituted or unsubstituted isoquinoline, a substituted or unsubstituted quinoxaline, a substituted or unsubstituted quinazoline, a substituted or unsubstituted carbazole, a substituted or unsubstituted phenazine, or a substituted or unsubstituted phenanthroline.

In some embodiments, in Chemical Formula 1, X may be one of Se and Te.

In some embodiments, in Chemical Formula 1, $Ar^2$ may be a cyclic group represented by Chemical Formula 3.

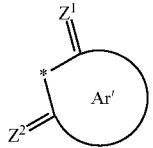

[Chemical Formula 3]

In some embodiments, in In Chemical Formula 3,
$Ar^1$ is a substituted or unsubstituted C6 to C30 aryl group or a substituted or unsubstituted C3 to C30 heteroaryl group,
$Z^1$ is O, S, Se, or Te, and
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group.

In some embodiments, in Chemical Formula 1, $Ar^2$ may be a cyclic group represented by one of Chemical Formula 4A to Chemical Formula 4F.

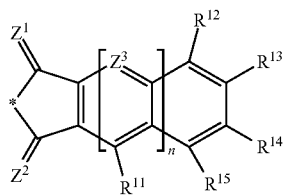

[Chemical Formula 4A]

In Chemical Formula 4A,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group,
$Z^3$ is N or $CR^c$ (wherein $R^c$ is hydrogen, deuterium, or a substituted or unsubstituted C1 to C10 alkyl group),
$R^{11}$, $R^{12}$, $R^{13}$, $R^{14}$, and $R^{15}$ are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, wherein $R^{11}$, $R^{12}$, $R^{13}$, $R^{14}$, and $R^{15}$ are independently present or at least one of $R^{12}$ and $R^{13}$ and $R^{14}$ and $R^{15}$ is linked with each other to provide a fused aromatic ring,
n is 0 or 1, and
* is a linking position.

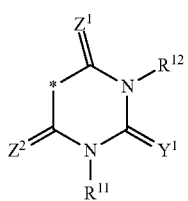

[Chemical Formula 4B]

In Chemical Formula 4B,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group,
$Y^1$ is O, S, Se, Te, or $C(R^a)(CN)$ (wherein $R^a$ is hydrogen, a cyano group (—CN), or a C1 to C10 alkyl group),
$R^{11}$ and $R^{12}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, cyano group (—CN), or a combination thereof, and
* is a linking position.

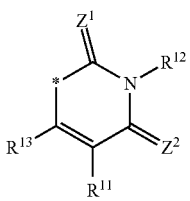

[Chemical Formula 4C]

In Chemical Formula 4C,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group,
$R^{11}$, $R^{12}$, and $R^{13}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, and
* is a linking position.

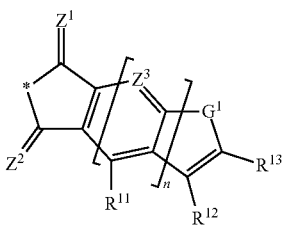

[Chemical Formula 4D]

In Chemical Formula 4D,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group,
$Z^3$ is N or $CR^c$ (wherein $R^c$ is hydrogen or a substituted or unsubstituted C1 to C10 alkyl group),
$G^1$ is O, S, Se, Te, $SiR^xR^y$, or $GeR^zR^w$, wherein $R^x$, $R^y$, $R^z$, and $R^w$ are independently hydrogen, a halogen, a substituted or unsubstituted C1 to C10 alkyl group, or a substituted or unsubstituted C6 to C10 aryl group, $R^{11}$, $R^{12}$, and $R^{13}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, wherein $R^{12}$ and $R^{13}$ are independently different and are linked with each other to provide a fused aromatic ring, n is 0 or 1, and

* is a linking position.

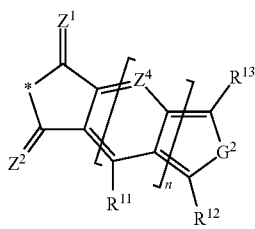

[Chemical Formula 4E]

In Chemical Formula 4E, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $G^2$ is O, S, Se, Te, $SiR^xR^y$, or $GeR^zR^w$, wherein $R^x$, $R^y$, $R^z$, and $R^w$ are independently hydrogen, a halogen, a substituted or unsubstituted C1 to C10 alkyl group, or a substituted or unsubstituted C6 to C10 aryl group, $R^{11}$, $R^{12}$, and $R^{13}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, n is 0 or 1, and

* is a linking position.

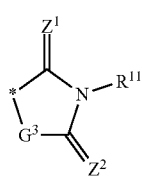

[Chemical Formula 4F]

In Chemical Formula 4F, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $R^{11}$ is hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^3$ is O, S, Se, Te, $SiR^xR^y$, or $GeR^zR^w$, wherein $R^x$, $R^y$, $R^z$, and $R^w$ are independently hydrogen, a halogen, a substituted or unsubstituted C1 to C10 alkyl group, or a substituted or unsubstituted C6 to C10 aryl group.

In some embodiments, the compound of Chemical Formula 1 may be one of the compounds represented by Chemical Formulae 5A to 5D.

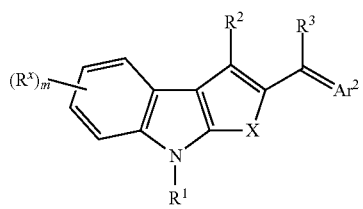

[Chemical Formula 5A]

In Chemical Formula 5A, $Ar^2$, X, and $R^1$ to $R^3$ are the same as in Chemical Formula 1, $R^x$ is hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —$SiR^aR^bR^c$ (wherein $R^a$, $R^b$, and $R^c$ are independently hydrogen or a substituted or unsubstituted C1 to C10 alkyl group), or a combination thereof, and m is an integer of 1 to 4.

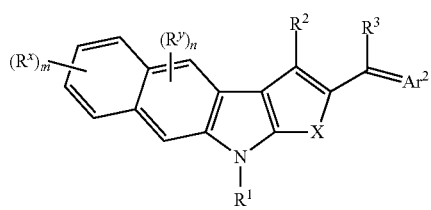

[Chemical Formula 5B]

In Chemical Formula 5B, $Ar^2$, X, and $R^1$ to $R^3$ are the same as in Chemical Formula 1, $R^x$ and $R^y$ are hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —$SiR^aR^bR^c$ (wherein $R^a$, $R^b$, and $R^c$ are independently hydrogen or a substituted or unsubstituted C1 to C10 alkyl group), or a combination thereof, m is an integer of 1 to 4, and n is an integer of 1 or 2.

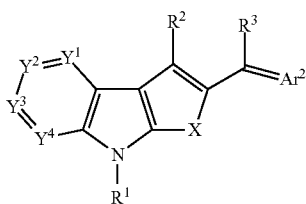

[Chemical Formula 5C]

In Chemical Formula 5C,

Ar$^2$, X, and R$^1$ to R$^3$ are the same as in Chemical Formula 1, and

Y$^1$ to Y$^4$ are independently CR$^x$R$^y$ or NR$^z$ (wherein R$^x$, R$^y$, and R$^z$ are hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ are independently hydrogen or a substituted or unsubstituted C1 to C10 alkyl group), or a combination thereof, provided that at least one of Y$^1$ to Y$^4$ is NR$^z$.

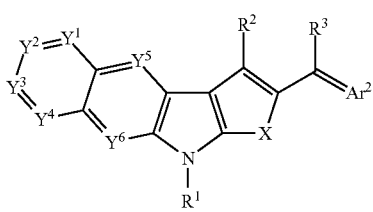

[Chemical Formula 5D]

In Chemical Formula 5D,

Ar$^2$, X, and R$^1$ to R$^3$ are the same as in Chemical Formula 1, and

Y$^1$ to Y$^4$ are independently CR$^x$R$^y$ or NR$^z$ (wherein R$^x$, R$^y$, and R$^z$ are hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ are independently hydrogen or a substituted or unsubstituted C1 to C10 alkyl group), or a combination thereof, provided that at least one of Y$^1$ to Y$^4$ is NR$^z$, Y$^5$ and Y$^6$ are independently CR$^x$R$^y$ or NR$^z$ (wherein R$^x$, R$^y$, and R$^z$ are hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ are independently hydrogen or a substituted or unsubstituted C1 to C10 alkyl group), or a combination thereof.

In some embodiments, the compound may have a maximum absorption wavelength ($\lambda_{max}$) in a wavelength range of about 500 nm to about 600 nm in a thin film state.

In some embodiments, the compound may exhibit an absorption curve having a full width at half maximum (FWHM) of about 50 nm to about 150 nm in a thin film state.

In some embodiments, a difference between a melting point of the compound and a temperature at which 10 wt % of an initial weight is lost (deposition temperature) may be greater than or equal to about 10° C.

According to another embodiment, a photoelectric device (e.g., organic photoelectric device) includes a first electrode and a second electrode facing each other and an active layer between the first electrode and the second electrode and including the compound represented by Chemical Formula 1.

According to another embodiment, an image sensor includes the photoelectric device.

In some embodiments, the image sensor may include a semiconductor substrate. The photoelectric device may be on the semiconductor substrate and selectively sensing light in a green wavelength region. The semiconductor substrate may be integrated with a plurality of first photo-sensing devices sensing light in a blue wavelength region and a plurality of second photo-sensing devices sensing light in a red wavelength region.

In some embodiments, the first photo-sensing device and the second photo-sensing device may be stacked in a vertical direction in the semiconductor substrate.

In some embodiments, the image sensor may further include a color filter layer including a blue filter selectively transmitting light in a blue wavelength region and a red filter selectively transmitting light in a red wavelength region.

In some embodiments, the photoelectric device may be a green photoelectric device. The image sensor may include a blue photoelectric device selectively absorbing light in a blue wavelength region and a red photoelectric device selectively absorbing light in a red wavelength region. The green photoelectric device, the blue photoelectric device, and the red photoelectric device may be stacked.

According to another embodiment, an electronic device includes the image sensor.

The compound may selectively absorb light in a green wavelength region and may have thermal stability and charge mobility. The compound improves efficiency of the device by increasing wavelength selectivity of the green wavelength region and provides photoelectric devices, image sensors and electronic devices that do not deteriorate performance even at high temperature processes due to improved thermal stability.

DETAILED DESCRIPTION

Figure 1:
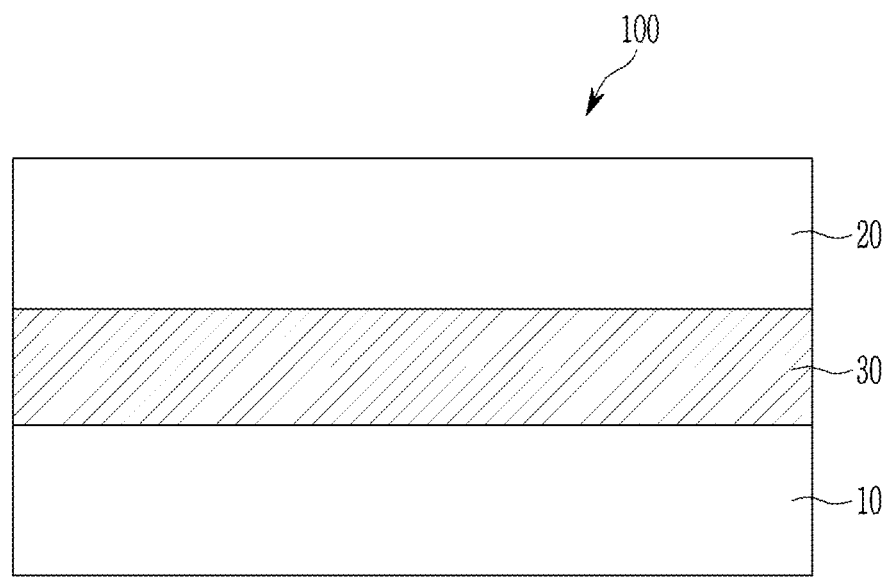
FIG. 1 is a cross-sectional view showing a photoelectric device according to an embodiment.

Example embodiments will hereinafter be described in detail, and may be easily performed by a person having an ordinary skill in the related art. However, this disclosure may be embodied in many different forms and is not to be construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

As used herein, "at least one of A, B, or C," "one of A, B, C, or a combination thereof" and "one of A, B, C, and a combination thereof" refer to each constituent element, and a combination thereof (e.g., A; B; A and B; A and C; B and C; or A, B, and C).

As used herein, when specific definition is not otherwise provided, "substituted" refers to replacement of a hydrogen of a compound or a functional group by a substituent selected from a halogen atom (F, Br, Cl, or I), a hydroxy group, a nitro group, a cyano group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C1 to C20 alkoxy group, a C2 to C20 alkenyl group, a C2 to C20 alkynyl group, a C6 to C30 aryl group, a C7 to C30 arylalkyl group, a C2 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof.

As used herein, when specific definition is not otherwise provided, "hetero" refers to one including 1 to 3 heteroatoms selected from N, O, S, Se, Te, P, and Si.

As used herein, "alkyl group" refers to a monovalent linear or branched saturated hydrocarbon group, for example a methyl group, an ethyl group, a propyl group, an isopropyl group, an n-butyl group, an isobutyl group, a t-butyl group, a pentyl group, a hexyl group, and the like.

As used herein, "cycloalkyl group" refers to a monovalent hydrocarbon cyclic group in which the atoms of the cycle are carbon, for example a cyclopropyl group, a cyclobutyl group, a cyclopentyl group, or a cyclohexyl group.

As used herein, "aryl group" refers to a substituent including all element of the functional group having p-orbitals which form conjugation, and may be a monocyclic, polycyclic or fused ring polycyclic (e.g., rings sharing adjacent pairs of carbon atoms) functional group.

As used herein, when a definition is not otherwise provided, "cyano-containing group" refers to a monovalent group such as a C1 to C30 alkyl group, a C2 to C30 alkenyl group, or a C2 to C30 alkynyl group where at least one hydrogen is substituted with a cyano group. The cyano-containing group also refers to a divalent group such as =$CR^{x'}$—$(CR^{x}R^{y})_p$—$CR^{y'}(CN)_2$ wherein $R^x$, $R^y$, $R^{x'}$, and $R^{y'}$ are independently hydrogen or a C1 to C10 alkyl group and p is an integer of 0 to 10 (or 1 to 10). Specific examples of the cyano-containing group may be a dicyanomethyl group, a dicyanovinyl group, a cyanoethynyl group, and the like. As used herein, the cyano-containing group does not include a functional group including a cyano group (—CN) alone.

As used herein, when a definition is not otherwise provided, "combination thereof" refers to at least two substituents bound to each other by a single bond or a C1 to C10 alkylene group, or at least two fused substituents. In addition, "combination" may also mean a stacked structure, a mixture, or an alloy.

As used herein, "hydrocarbon cyclic group" refers to a fused ring of an aromatic ring (arene ring) and a nonaromatic ring (alicyclic ring) and may include, for example a fused ring which is formed by linking at least one aromatic ring (arene ring) such as a C6 to C30 aryl group, a C6 to C20 aryl group, or a C6 to C10 aryl group with at least one nonaromatic ring (alicyclic ring) such as a C3 to C30 cycloalkyl group, a C3 to C20 cycloalkyl group, or a C3 to C10 cycloalkyl group.

As used herein, "heterocyclic group" refers to a cyclic group including a heteroatom selected from N, O, S, Se, Te, P, and Si instead of 1 to 3 carbon atoms in a cyclic group selected from an arene group (e.g., C6 to C30 aryl group, C6 to C20 aryl group or C6 to C10 aryl group), an alicyclic hydrocarbon group (e.g., C3 to C30 cycloalkyl group, C3 to C20 cycloalkyl group or C3 to C10 cycloalkyl group), or a fused ring thereof. At least one carbon atom of the heterocyclic group may also be substituted with a thiocarbonyl group (C=S).

As used herein, "arene group" refers to a hydrocarbon group having an aromatic ring, and includes monocyclic and polycyclic hydrocarbon groups, and the additional ring of the polycyclic hydrocarbon group may be an aromatic ring or a nonaromatic ring. "Heteroarene group" refers to an arene group including 1 to 3 heteroatoms selected from N, O, S, Se, Te, P and Si in a cyclic group.

As used herein, "C6 to C30 aromatic hydrocarbon group" includes a C6 to C30 aryl group such as a phenyl group, a naphthyl group, a C6 to C30 arylene group, and the like, but is not limited thereto.

As used herein, "aliphatic hydrocarbon group" may include, for example, a C1 to C15 alkyl group such as a methyl group, an ethyl group, a propyl group, and the like, a C1 to C15 alkylene group, a C2 to C15 alkenyl group such as an ethenyl group or a propenyl group, a C2 to C15 alkynyl group such as an ethynyl group or a propynyl group, but is not limited to.

As used herein, "aromatic ring" refers to a C5 to C10 cyclic group (e.g., C6 to C12 aryl group) that provides a conjugated structure or a C2 to C10 heterocyclic group (e.g., C2 to C4 heteroaryl group) that provides a conjugated structure).

Hereinafter, a compound according to an embodiment is described. The compound is represented by Chemical Formula 1.

[Chemical Formula 1]

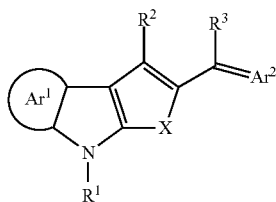

In Chemical Formula 1,

Ar$^1$ is a substituted or unsubstituted C6 to C30 arene group or a substituted or unsubstituted C3 to C30 heteroarene group, Ar$^2$ is a substituted or unsubstituted C6 to C30 hydrocarbon cyclic group having at least one functional group selected from C=O, C=S, C=Se, and C=Te, a substituted or unsubstituted C6 to C30 heterocyclic group having at least one functional group selected from C=O, C=S, C=Se, and C=Te, or a fused ring thereof, X is O, Se, Te, SiR$^a$R$^b$, or GeR$^c$R$^d$ (wherein R$^a$, R$^b$, R$^c$, and R$^d$ are independently hydrogen, deuterium, or a substituted or unsubstituted C1 to C10 alkyl group, wherein R$^a$, R$^b$, R$^c$, and R$^d$ are independently present or R$^a$ and R$^b$ or R$^c$ and R$^d$ are linked with each other to provide a spiro structure), and R$^1$ to R$^3$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ are independently hydrogen or a substituted or unsubstituted C1 to C10 alkyl group), or a combination thereof.

The compound represented by Chemical Formula 1 includes an electron donor moiety of an aromatic ring containing heteroatoms (N and X) and an electron acceptor moiety marked as Ar$^2$. In Chemical Formula 1, the electron donor moiety may induce a planar structure and thus improve charge mobility.

The compound represented by Chemical Formula 1 may have an aspect ratio (z/x) obtained by dividing the shortest length (z) by the longest length (x) in the molecular structure in a range of less than or equal to about 0.5, for example, less than or equal to about 0.4, or less than or equal to about 0.3. Within the range, the compound may maintain excellent planarity, and accordingly, the charge mobility thereof may be improved.

In Chemical Formula 1, the electron donor moiety of an aromatic ring containing hetero atoms (N and X) may increase the planarity by fusing greater than or equal to three aromatic rings and thus adjusting the aspect ratio to be smaller.

In Chemical Formula 1, R$^1$ to R$^3$ include no amine group. Accordingly, the structure of Chemical Formula 1 has a donor-acceptor structure, and accordingly, an absorption wavelength may be adjusted within a green wavelength range (greater than or equal to about 500 nm to less than or equal to about 600 nm, for example, greater than or equal to about 510 nm and less than or equal to about 570 nm, or greater than or equal to about 510 nm less than or equal to about 550 nm), a deposition temperature may be decreased, and an absorption coefficient may be increased.

In Chemical Formula 1, when X is SiR$^a$R$^b$ or GeR$^c$R$^d$, R$^a$, R$^b$, R$^c$, and R$^d$ may be independently present or may be linked with each other to provide a spiro structure. The spiro structure may be a C5 cycloalkyl group or a C6 cycloalkyl group.

In Chemical Formula 1, when X is SiR$^a$R$^b$ or GeR$^c$R$^d$ and R$^a$, R$^b$, R$^c$, and R$^d$ are linked with each other to provide a spiro structure, the compound represented by Chemical Formula 1 may be represented by Chemical Formula 2A or Chemical Formula 2B.

[Chemical Formula 2A]

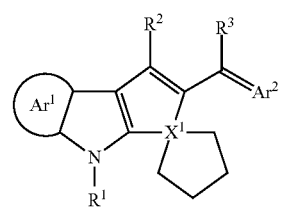

[Chemical Formula 2B]

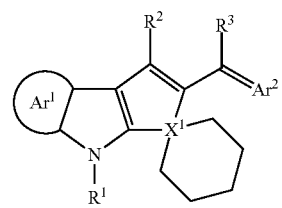

In Chemical Formulae 2A and 2B,

Ar$^1$, Ar$^2$, and R$^1$ to R$^3$ may be the same as in Chemical Formula 1,

X$^1$ may be Si or Ge, at least one hydrogen of the pentagonal ring or hexagonal ring of the spiro structure may be replaced by a group selected from deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ are independently hydrogen or a substituted or unsubstituted C1 to C10 alkyl group), and a combination thereof.

In Chemical Formula 1, Ar$^2$ may be represented by Chemical Formula 3.

[Chemical Formula 3]

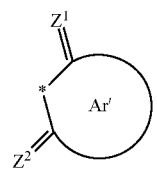

In Chemical Formula 3,

Ar' is a substituted or unsubstituted C6 to C30 aryl group or a substituted or unsubstituted C3 to C30 heteroaryl group, Z$^1$ is O, S, Se, or Te, and Z$^2$ is O, S, Se, Te, or CR$^a$R$^b$, wherein R$^a$ and R$^b$ are independently hydrogen, a substituted or unsubstituted C1 to C10 alkyl group, a cyano group, or a cyano-containing group, provided that when Z$^2$ is CR$^a$R$^b$, at least one of R$^a$ and R$^b$ is a cyano group or a cyano-containing group.

In Chemical Formula 1, Ar² may be a cyclic group represented by one of Chemical Formula 4A to Chemical Formula 4F.

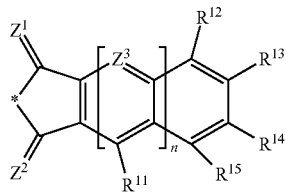

[Chemical Formula 4A]

In Chemical Formula 4A, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Z^3$ is N or $CR^c$ (wherein $R^c$ is hydrogen, deuterium, or a substituted or unsubstituted C1 to C10 alkyl group), $R^{11}$, $R^{12}$, $R^{13}$, $R^{14}$, and $R^{15}$ are the same or different and are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, wherein $R^{11}$, $R^{12}$, $R^{13}$, $R^{14}$, and $R^{15}$ are independently present or at least one of $R^{12}$ and $R^{13}$ and $R^{14}$ and $R^{15}$ is linked with each other to provide a fused aromatic ring, n is 0 or 1, and

* is a linking position.

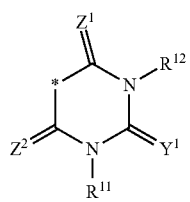

[Chemical Formula 4B]

In Chemical Formula 4B, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Y^1$ is O, S, Se, Te, or $C(R^a)(CN)$ (wherein $R^a$ is hydrogen, a cyano group (—CN), or a C1 to C10 alkyl group), $R^{11}$ and $R^{12}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking position.

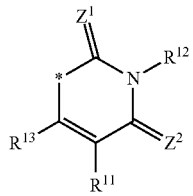

[Chemical Formula 4C]

In Chemical Formula 4C, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, and

* is a linking position.

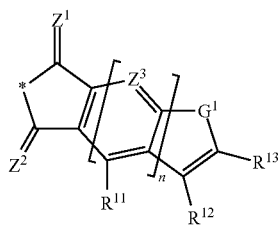

[Chemical Formula 4D]

In Chemical Formula 4D, $Z^1$ is O, S, Se, or Te, and $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Z^3$ is N or $CR^c$ (wherein $R^c$ is hydrogen or a substituted or unsubstituted C1 to C10 alkyl group), $G^1$ is O, S, Se, Te, $SiR^xR^y$, or $GeR^zR^w$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, wherein $R^{12}$ and $R^{13}$ are independently different and are linked with each other to provide a fused aromatic ring, n is 0 or 1, and

* is a linking position.

[Chemical Formula 4E]

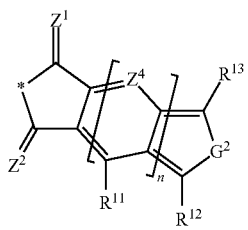

In Chemical Formula 4E, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $G^2$ is O, S, Se, Te, $SiR^xR^y$, or $GeR^zR^w$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, n is 0 or 1, and

* is a linking position.

[Chemical Formula 4F]

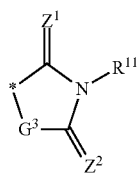

In Chemical Formula 4F, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $R^{11}$ is hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^3$ is O, S, Se, Te, $SiR^xR^y$, or $GeR^zR^w$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group.

The cyclic group represented by Chemical Formula 4A may be a cyclic group represented by Chemical Formula 4A-1 or Chemical Formula 4A-2.

[Chemical Formula 4A-1]

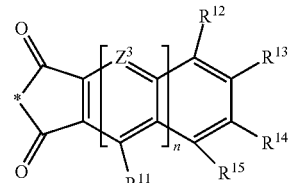

[Chemical Formula 4A-2]

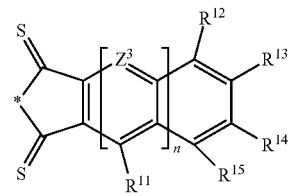

In Chemical Formula 4A-1 and Chemical Formula 4A-2, $Z^3$, $R^{11}$, n, $R^{11}$, $R^{12}$, $R^{13}$, $R^{14}$, and $R^{15}$ are the same as in Chemical Formula 4A.

When $R^{12}$ and $R^{13}$ and/or $R^{14}$ and $R^{15}$ are independently linked with each other to provide a fused aromatic ring, the cyclic group represented by Chemical Formula 4A may be a cyclic group represented by Chemical Formula 4A-3.

[Chemical Formula 4A-3]

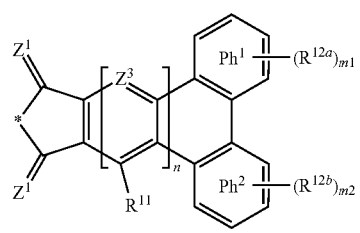

In Chemical Formula 4A-3, $Z^1$, $Z^2$, $Z^3$, $R^{11}$, and n are the same as in Chemical Formula 4A, $R^{12a}$ and $R^{12b}$ are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, m1 and m2 are independently integers of 0 to 4, Ph1 and Ph2 are fused phenylene rings and one of Ph1 and Ph2 may optionally be omitted.

The cyclic group represented by Chemical Formula 4B may be, for example, a cyclic group represented by Chemical Formula 4B-1, 4B-2, or 4B-3.

[Chemical Formula 4B-1]

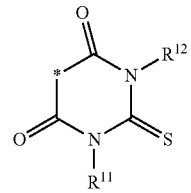

-continued

[Chemical Formula 4B-2]

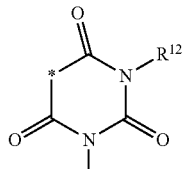

[Chemical Formula 4B-3]

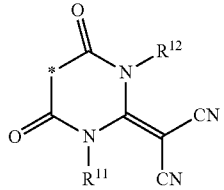

In Chemical Formula 4B-1, 4B-2, and 4B-3,
$R^{11}$ and $R^{12}$ are the same as in Chemical Formula 4B.

The cyclic group represented by Chemical Formula 4C may be, for example, a cyclic group represented by Chemical Formula 4C-1 or 4C-3.

[Chemical Formula 4C-1]

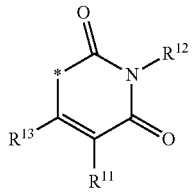

[Chemical Formula 4C-2]

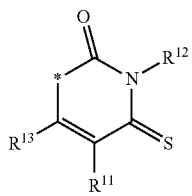

In Chemical Formulae 4C-1 and 4C-2,
$R^{11}$ to $R^{13}$ are the same as in Chemical Formula 4C.

In Chemical Formula 1, the heteroatoms (N and X) of the electron donor moiety and heteroatoms (O, S, Se, or Te) of the electron acceptor moiety ($Ar^2$) increase intramolecular interactions and thus the absorption intensity at a specific wavelength may be improved.

The compound of Chemical Formula 1 may be any one of the compounds represented by Chemical Formulae 5A to 5D.

[Chemical Formula 5A]

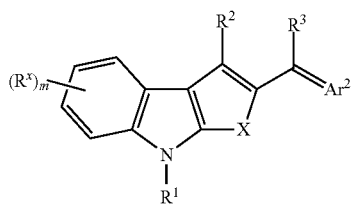

In Chemical Formula 5A,
$Ar^2$, X, and $R^1$ to $R^3$ are the same as in Chemical Formula 1, $R^x$ is hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —$SiR^aR^bR^c$ (wherein $R^a$, $R^b$, and $R^c$ are independently hydrogen or a substituted or unsubstituted C1 to C10 alkyl group), or a combination thereof, and
m is an integer of 1 to 4.

[Chemical Formula 5B]

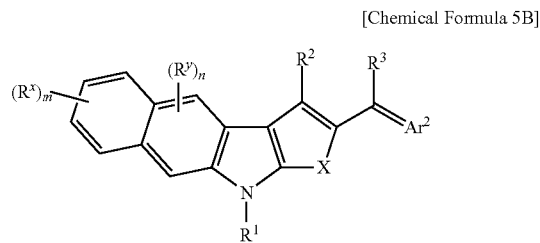

In Chemical Formula 5B,
$Ar^2$, X, and $R^1$ to $R^3$ are the same as in Chemical Formula 1, $R^x$ and $R^y$ are hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —$SiR^aR^bR^c$ (wherein $R^a$, $R^b$, and $R^c$ are independently hydrogen or a substituted or unsubstituted C1 to C10 alkyl group), or a combination thereof,
m is an integer of 1 to 4, and
n is an integer of 1 or 2.

[Chemical Formula 5C]

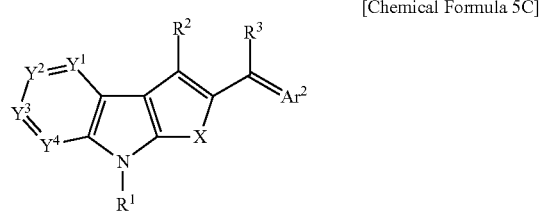

In Chemical Formula 5C,
$Ar^2$, X, and $R^1$ to $R^3$ are the same as in Chemical Formula 1, and $Y^1$ to $Y^4$ are independently $CR^xR^y$ or $NR^z$ (wherein $R^x$, $R^y$, and $R^z$ are hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —$SiR^aR^bR^c$ (wherein $R^a$, $R^b$, and $R^c$ are independently hydrogen or a substituted or unsubstituted C1 to C10 alkyl group), or a combination thereof, provided that at least one of $Y^1$ to $Y^4$ is $NR^z$.

[Chemical Formula 5D]

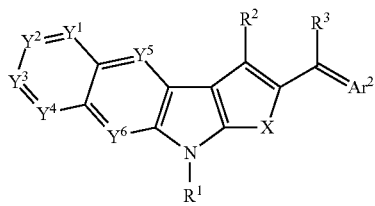

In Chemical Formula 5D, $Ar^2$, X, and $R^1$ to $R^3$ are the same as in Chemical Formula 1, $Y^1$ to $Y^4$ are independently $CR^xR^y$ or $NR^z$ (wherein $R^x$, $R^y$, and $R^z$ are hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —$SiR^aR^bR^c$ (wherein $R^a$, $R^b$, and $R^c$ are independently hydrogen or a substituted or unsubstituted C1 to C10 alkyl group), or a combination thereof, provided that at least one of $Y^1$ to $Y^4$ is $NR^z$, and $Y^5$ and $Y^6$ are independently $CR^xR^y$ or $NR^z$ (wherein $R^x$, $R^y$, and $R^z$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —$SiR^aR^bR^c$ (wherein $R^a$, $R^b$, and $R^c$ are independently hydrogen or a substituted or unsubstituted C1 to C10 alkyl group), or a combination thereof.

Specific examples of the compound of Chemical Formula 1 may include, but are not limited to, compounds of Chemical Formula 6A, Chemical Formula 6B, Chemical Formula 6C, Chemical Formula 6D, Chemical Formula 6E, and Chemical Formula 6F.

[Chemical Formula 6A]

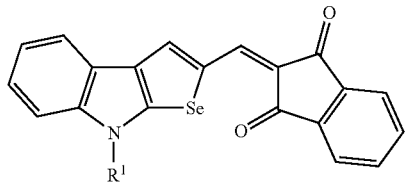

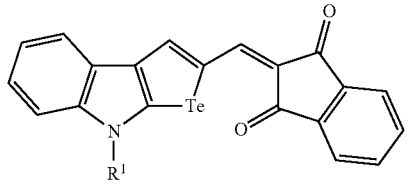

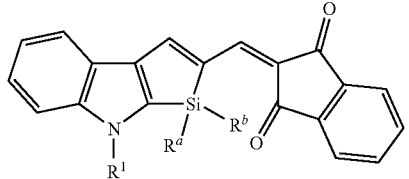

-continued

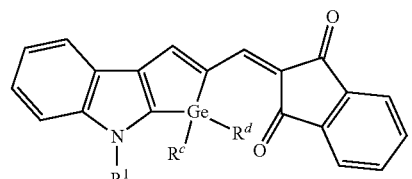

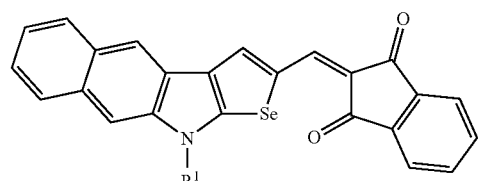

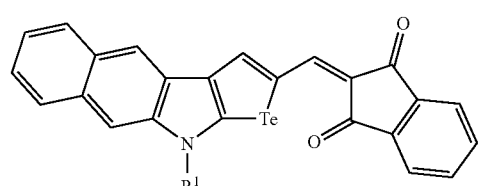

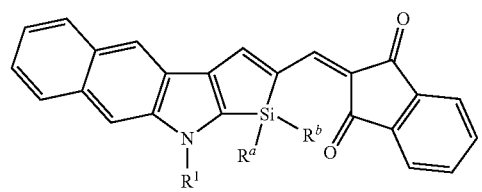

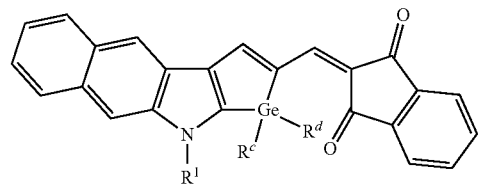

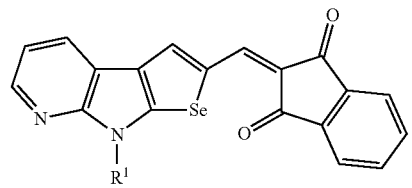

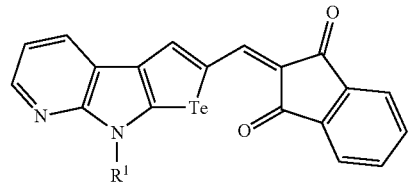

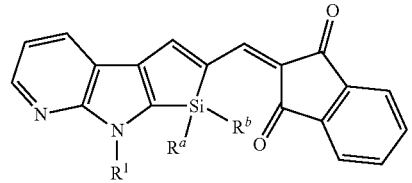

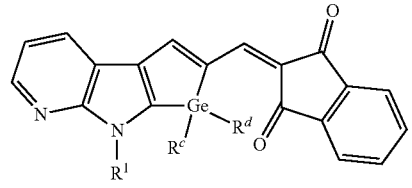

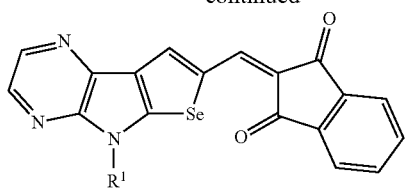
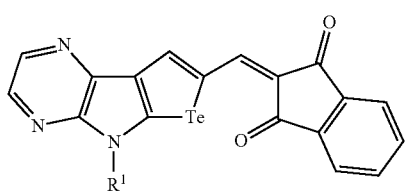
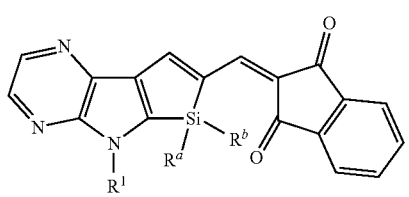
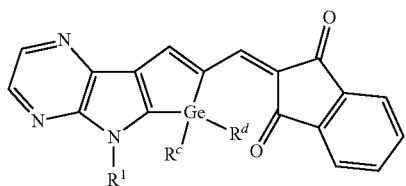
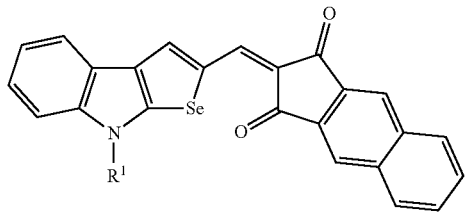
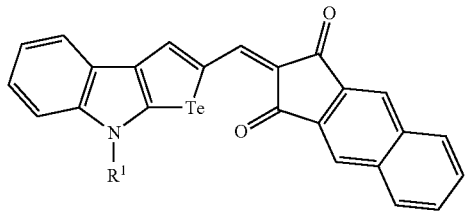
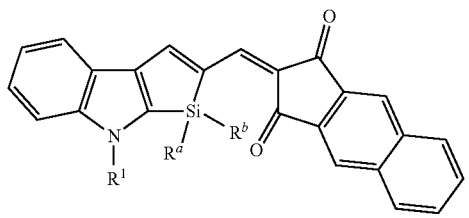
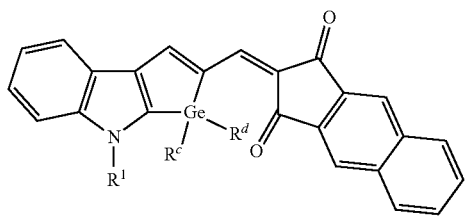
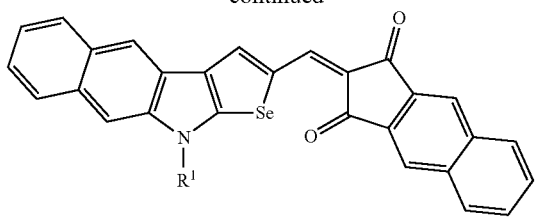
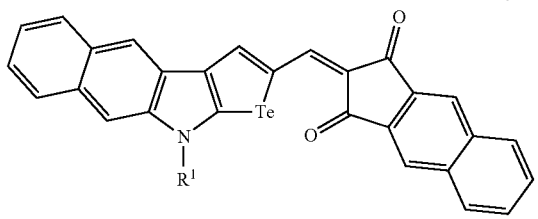
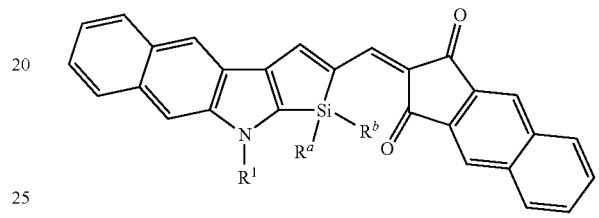
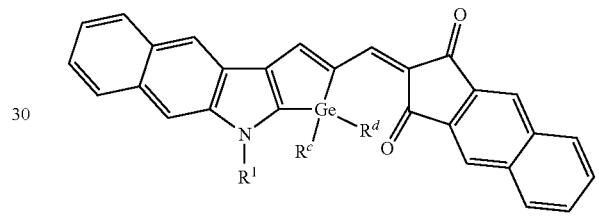
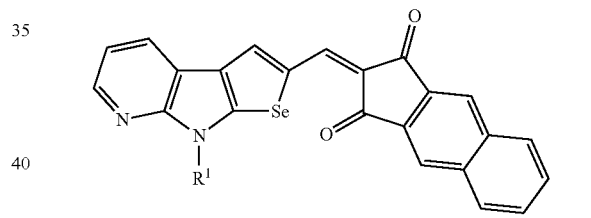
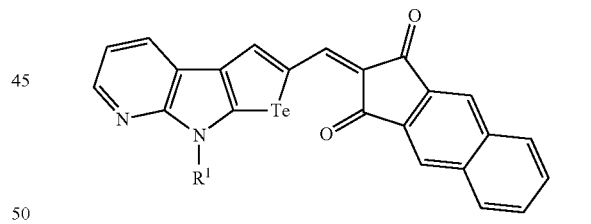
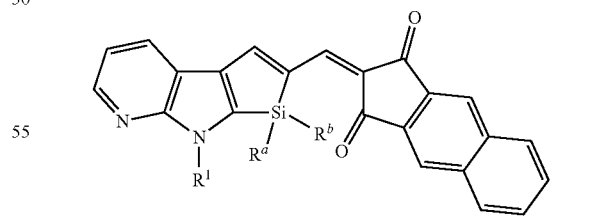
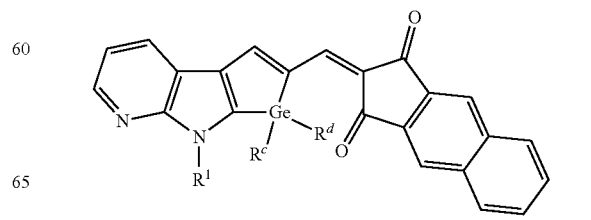

-continued

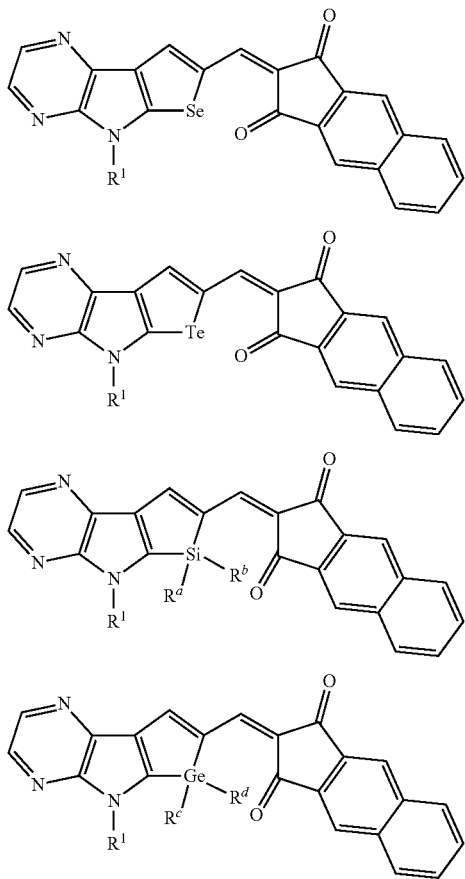

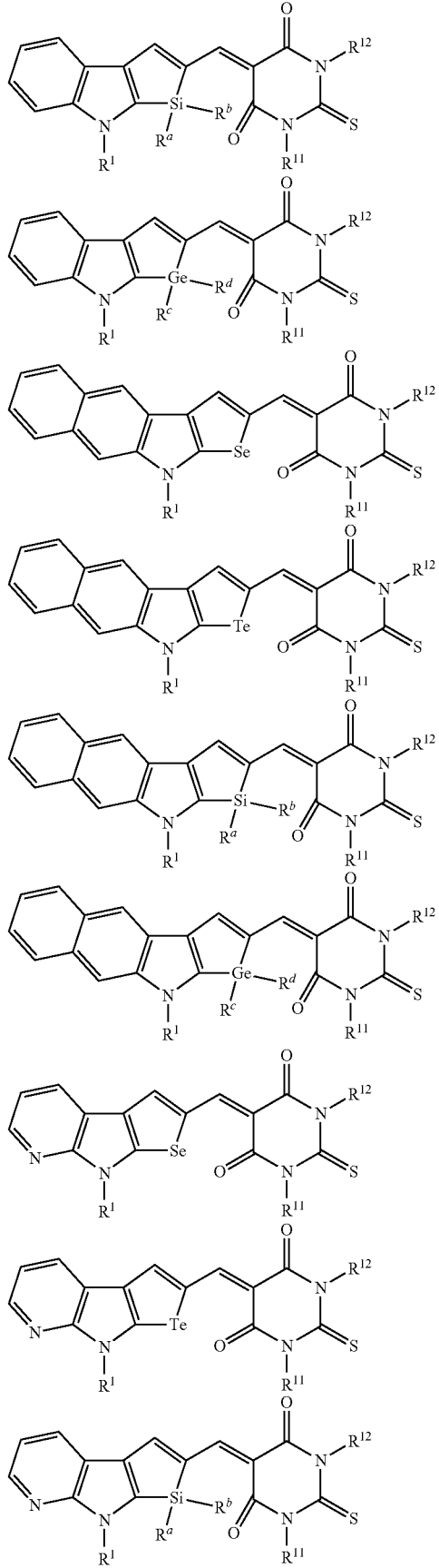

In Chemical Formula 6A,

R¹, $R^a$, $R^b$, $R^c$, and $R^d$ are the same as in Chemical Formula 1, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

[Chemical Formula 6B]

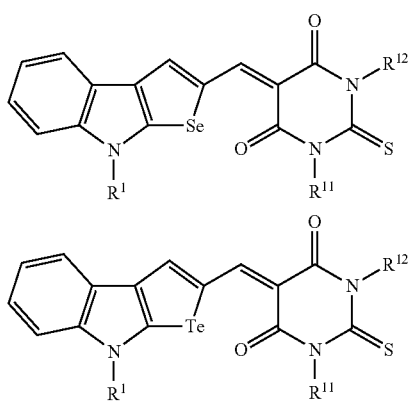

25
-continued
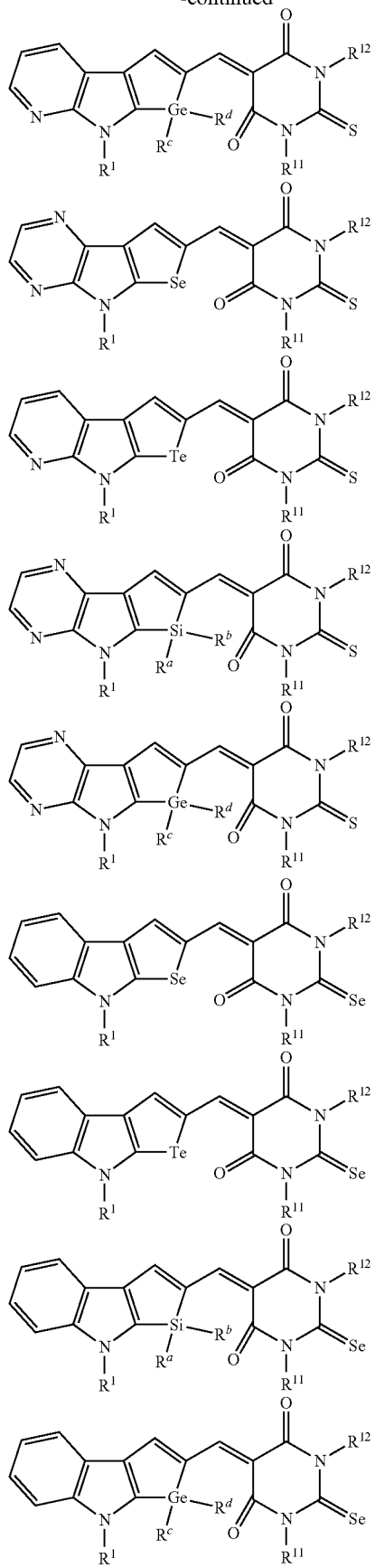
26
-continued
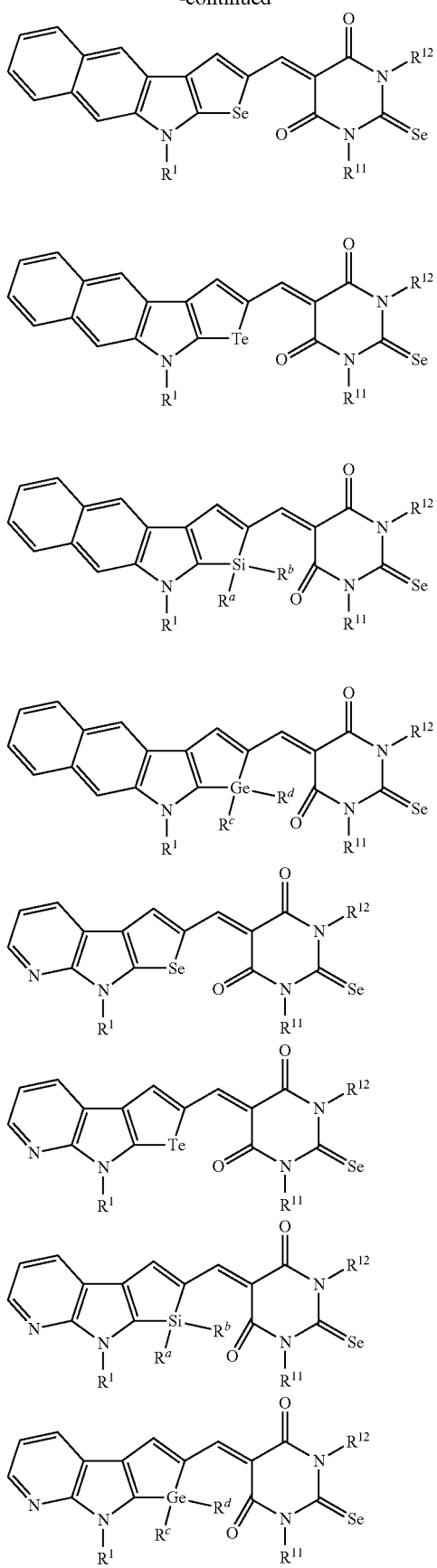

-continued

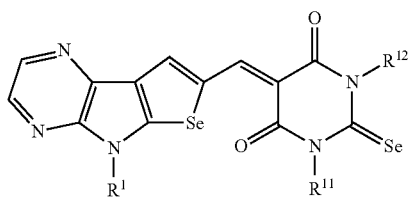

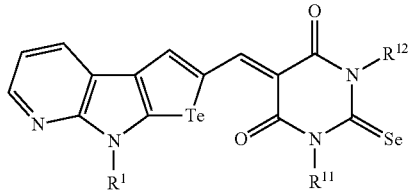

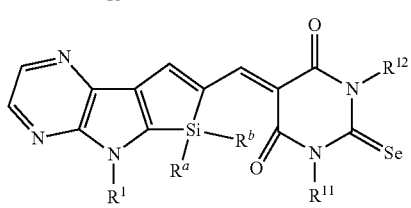

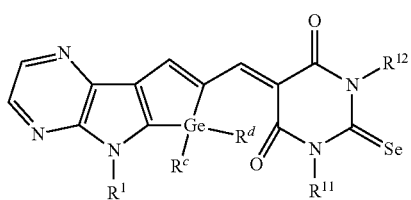

In Chemical Formula 6B, $R^1$, $R^a$, $R^b$, $R^c$, and $R^d$ are the same as in Chemical Formula 1, $R^{11}$ and $R^{12}$ are the same as in Chemical Formula 4B, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

[Chemical Formula 6C]

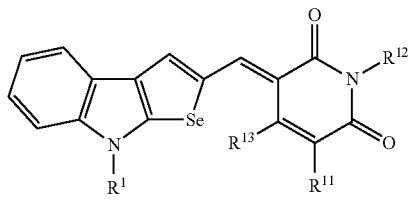

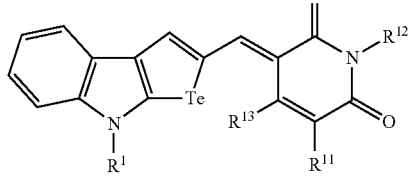

-continued

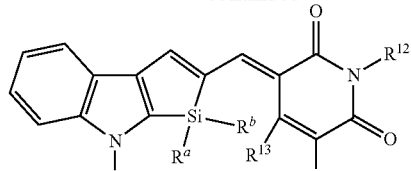

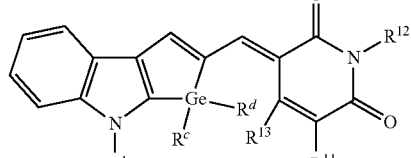

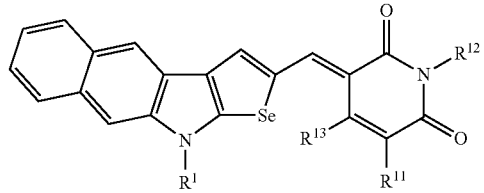

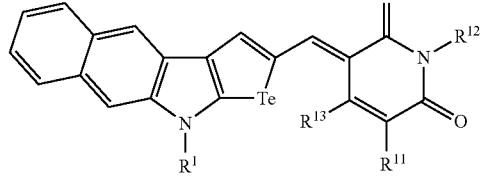

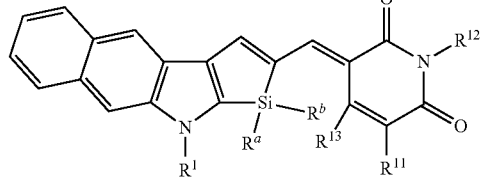

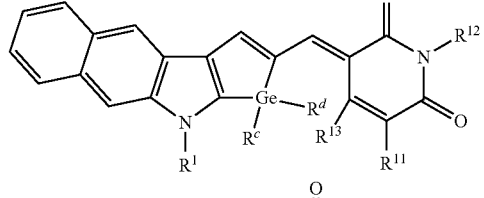

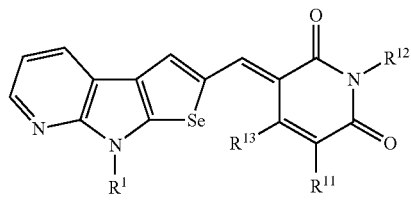

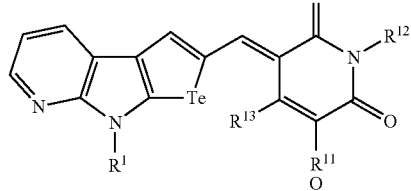

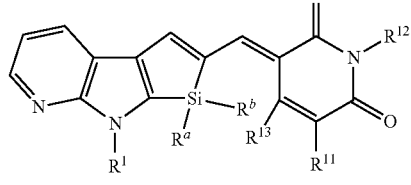

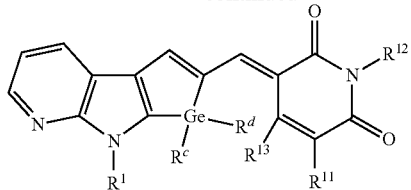

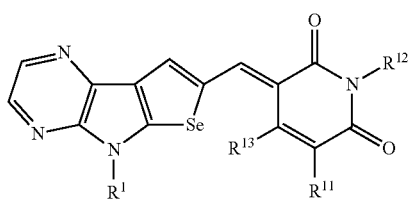

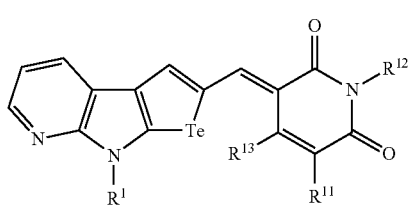

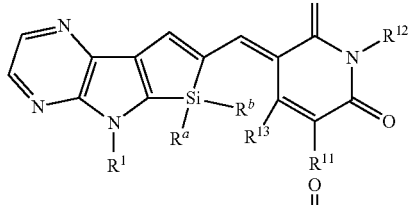

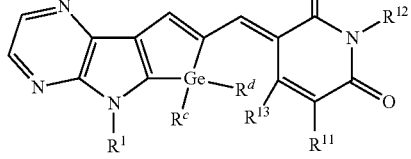

In Chemical Formula 6C, $R^1$, $R^a$, $R^b$, $R^c$, and $R^d$ are the same as in Chemical Formula 1, $R^{11}$ to $R^{13}$ are the same as in Chemical Formula 4C, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

[Chemical Formula 6D]

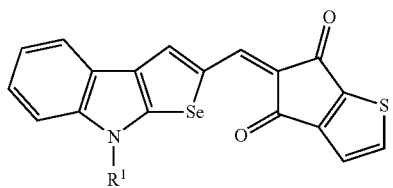

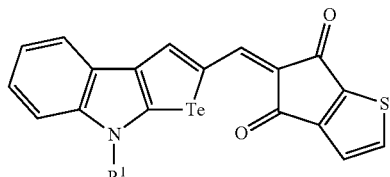

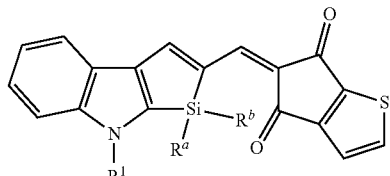

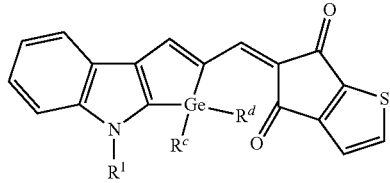

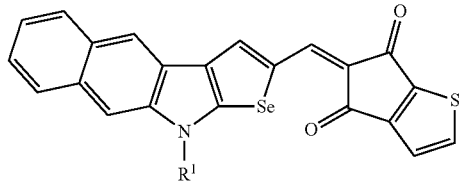

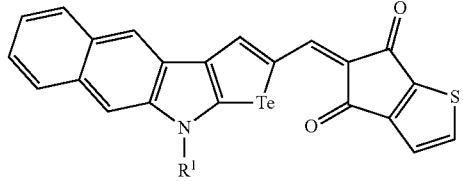

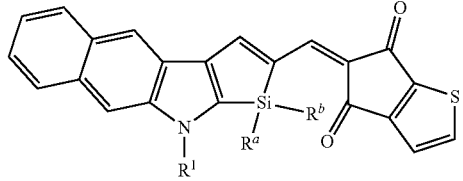

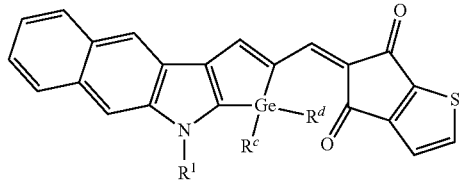

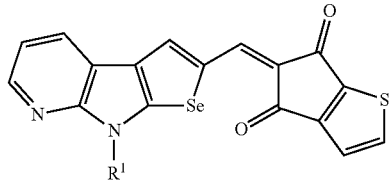

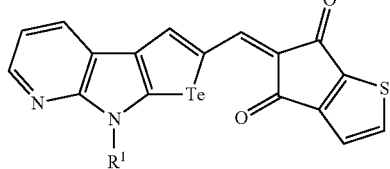

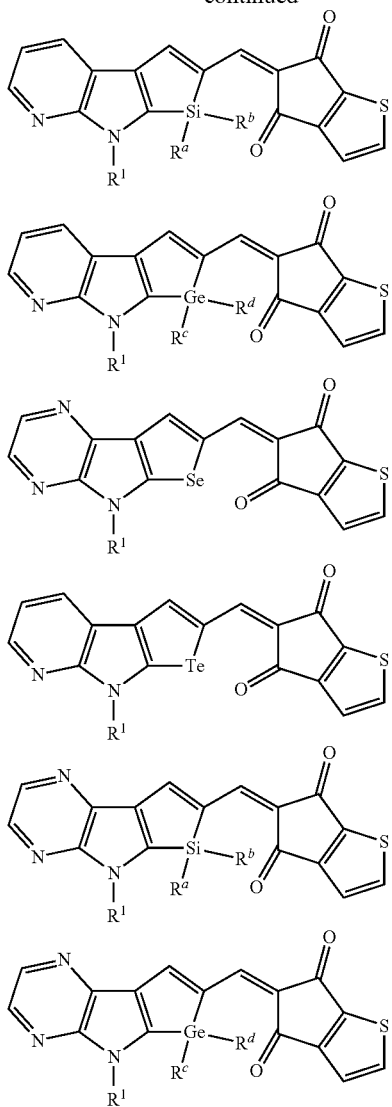

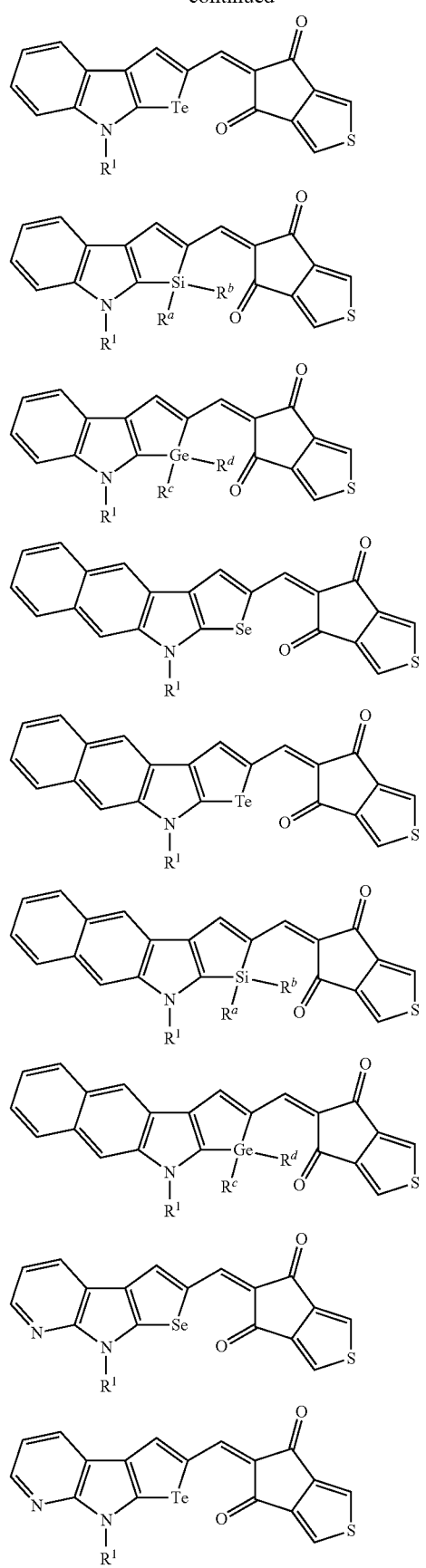

In Chemical Formula 6D, $R^1$, $R^a$, $R^b$, $R^c$, and $R^d$ are the same as in Chemical Formula 1, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

[Chemical Formula 6E]

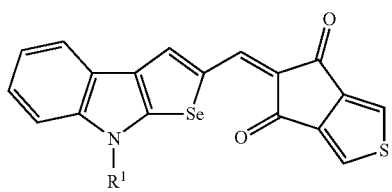

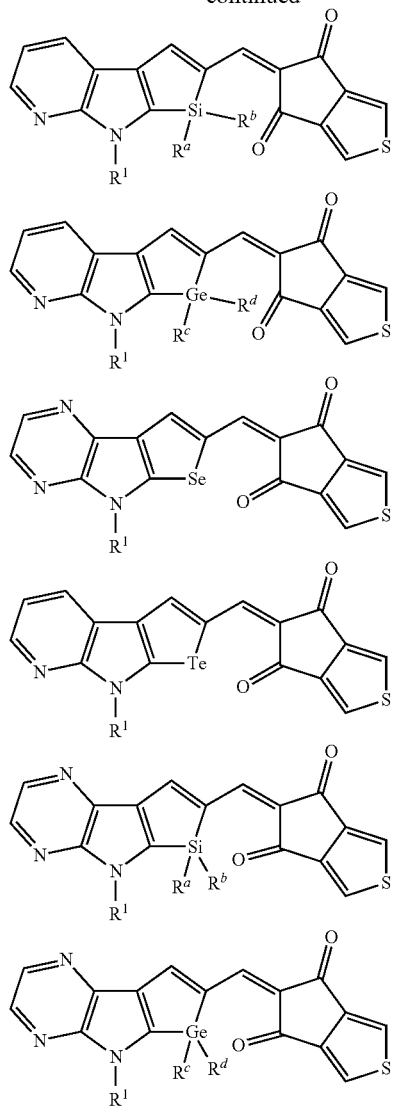

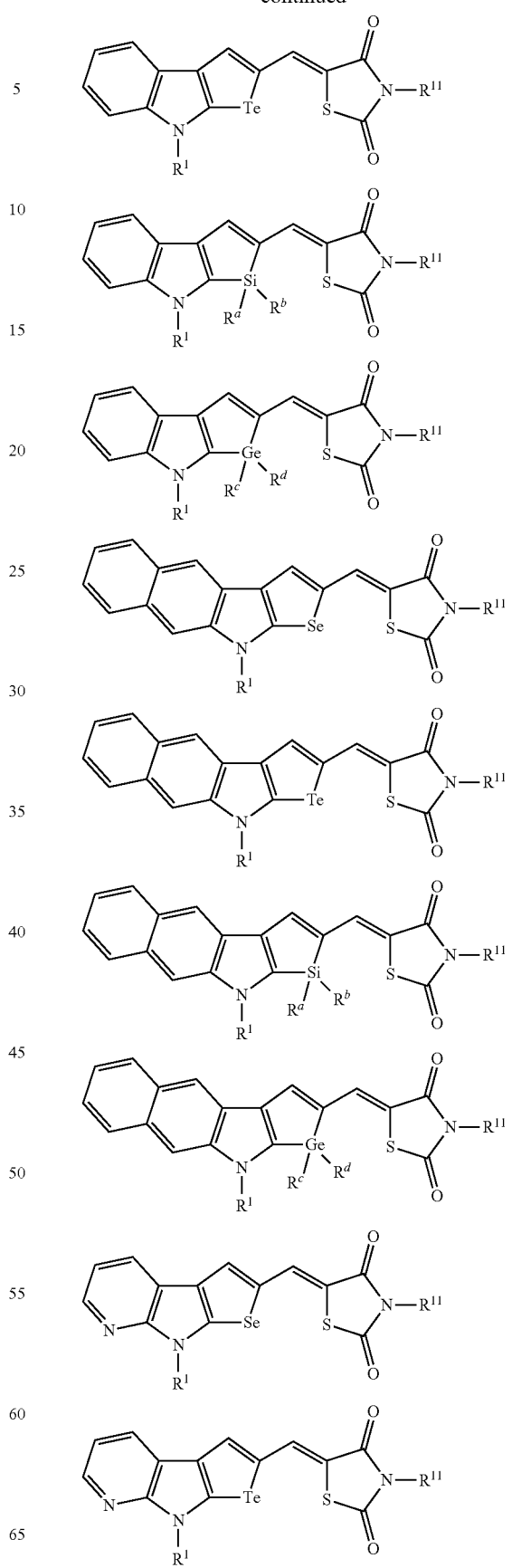

In Chemical Formula 6E, $R^1$, $R^a$, $R^b$, $R^c$, and $R^d$ are the same as in Chemical Formula 1, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

[Chemical Formula 6F]

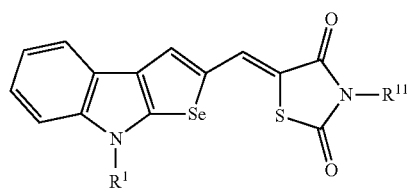

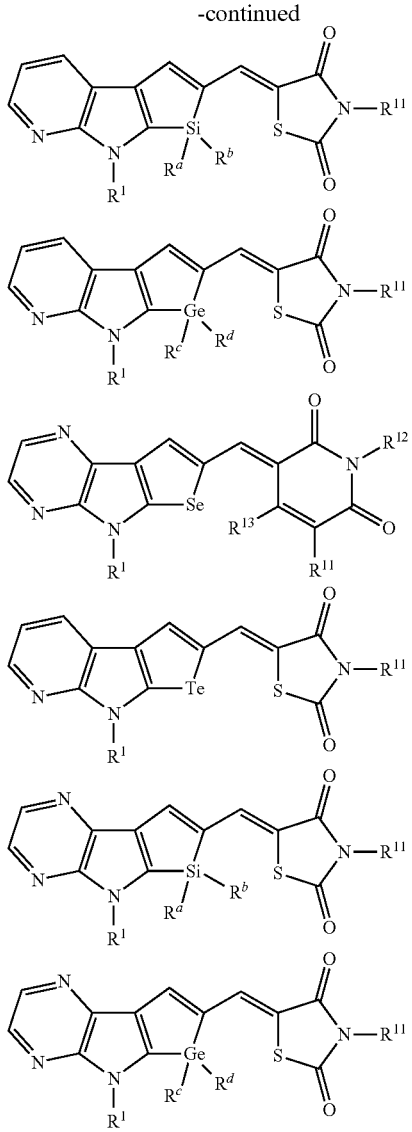

In Chemical Formula 6F,

R[11] is the same as in Chemical Formula 4F

R[1], R[a], R[b], R[c], and R[d] are the same as in Chemical Formula 1, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

The compound is a compound selectively absorbing light in a green wavelength region, and may have a maximum absorption wavelength ($\lambda_{max}$) in a wavelength region of about 500 nm to about 600 nm, for example about 510 nm to about 570 nm, or about 510 nm to about 550 nm.

The compound may exhibit a light absorption curve having a full width at half maximum (FWHM) of about 50 nm to about 150 nm. Herein, the FWHM is a width of a wavelength corresponding to half of a maximum absorption point. As used herein, when specific definition is not otherwise provided, it may be defined by absorbance measured by UV-Vis spectroscopy. When the full width at half maximum (FWHM) is within the range, selectivity in a green wavelength region may be increased. The thin film may be a thin film deposited under a vacuum condition.

The compound may be formed into a thin film by a deposition method. The deposition method may provide a uniform thin film and have small inclusion possibility of impurities into the thin film, but when the compound has a lower melting point than a temperature for the deposition, a product decomposed from the compound may be deposited and thus performance of a device may be deteriorated. Accordingly, the compound desirably has a higher melting point than the deposition temperature. In this regard, the compound has a melting point higher than the deposition temperature, for example, about 10° C. or higher, about 15° C. or higher, about 20° C. or higher, about 25° C. or higher, or about 30° C. or higher, and thus may be desirably used in the deposition process.

In more detail, the donor-acceptor-type material represented by the structure of Chemical Formula 1 may be thermally decomposed at the melting point ($T_m$) of the material because the melting point ($T_m$) is similar to the decomposition temperature ($T_d$). If the temperature (sublimation temperature, deposition temperature, $T_s$) at which a film is formed by vacuum deposition is higher than $T_m$, decomposition occurs more preferentially than sublimation (deposition), and thus a normal device cannot be produced. Since such a material cannot produce a stable image sensor, $T_m$ should be higher than $T_s$, and $T_m - T_s \geq 10°$ C. is more desirable.

In addition, a micro lens array (MLA) needs to be formed to concentrate light after manufacturing an organic photoelectric device during production of an image sensor. This micro lens array requires a relatively high temperature (greater than or equal to about 160° C., for example greater than or equal to about 170° C., greater than or equal to about 180° C., or greater than or equal to about 190° C.). The performance of the photoelectric devices (e.g., organic photoelectric devices) is required not to be deteriorated in these heat-treatment processes. The performance deterioration of the organic photoelectric device during the heat treatment of MLA may be caused not by chemical decomposition of an organic material but its morphology change. The morphology change is in general caused, when a material starts a thermal agitation due to a heat treatment, but even a material having a firm molecule structure may not have the thermal agitation and be prevented from the deterioration by the heat treatment. The compound may be suppressed from the thermal vibration of molecules due to a conjugation structure in the donor moiety and thus may be stably maintained during the MLA heat treatment and secure process stability.

The compound may be a p-type semiconductor compound.

Since the compound works as a p-type semiconductor, the compound may be appropriately used, as long as it has a higher LUMO energy level than an n-type semiconductor. For example, when the compound is mixed with an n-type material such as fullerene, the compound desirably has a higher LUMO energy level than 4.2 eV than the fullerene having a LUMO energy level of 4.2 eV. As for the appropriate HOMO-LUMO energy level of the compound, when the compound has a HOMO energy level ranging from about 5.2 eV to about 6.1 eV, and an energy bandgap ranging from about 2.0 eV to about 3.0 eV, the LUMO energy level of the compound is in a range of about 3.0 eV to about 3.2 eV. The compound having a HOMO energy level, an LUMO energy level, and an energy bandgap within the ranges may be used as a p-type semiconductor compound effectively absorbing light in a green wavelength region, and thus has high external quantum efficiency (EQE) and resultantly improves photoelectric conversion efficiency.

In example embodiments, in view of a thin film formation, a stably depositable compound is desirable and thus the compound has a molecular weight of about 300 g/mol to about 1500 g/mol. However, even though the compound has a molecular weight out of the range, a depositable compound may be used without limitation. In addition, when the compound is formed to form a thin film using a coating process, a compound that is dissolved in a solvent and coated may be used without limitation.

Hereinafter, a photoelectric device including the compound according to an embodiment is described with reference to drawings.

FIG. 1 is a cross-sectional view showing a photoelectric device according to an embodiment.

Referring to FIG. 1, a photoelectric device 100 according to an example embodiment includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor such as indium tin oxide (ITO) or indium zinc oxide (IZO), or a metal thin layer of a thin single layer or multilayer. When one of the first electrode 10 and the second electrode 20 is a non-light-transmitting electrode, it may be made of, for example, an opaque conductor such as aluminum (Al).

The active layer 30 includes a p-type semiconductor and an n-type semiconductor to form a pn junction, and absorbs external light to generate excitons and then separates the generated excitons into holes and electrons.

The active layer 30 includes the compound represented by Chemical Formula 1. The compound may act as a p-type semiconductor compound in the active layer 30.

The compound is a compound selectively absorbing light in a green wavelength region, and the active layer 30 including the compound may have a maximum absorption wavelength ($\lambda_{max}$) in a wavelength region of about 500 nm to about 600 nm, for example about 510 nm to about 570 nm.

The active layer 30 may exhibit a light absorption curve having a relatively narrow full width at half maximum (FWHM) of about 50 nm to about 120 nm, about 50 nm to about 110 nm, or about 50 nm to about 100 nm. Accordingly, the active layer 30 has high selectivity for light in a green wavelength region.

The active layer may have an absorption coefficient of greater than or equal to about $5.5 \times 10^4$ cm$^{-1}$, for example about $5.8 \times 10^4$ cm$^{-1}$ to about $10 \times 10^4$ cm$^{-1}$ or about $7.0 \times 10^4$ cm$^{-1}$ to about $10 \times 10^4$ cm$^{-1}$.

The active layer 30 may further include an n-type semiconductor compound for forming pn junction.

The n-type semiconductor compound may be sub-phthalocyanine or a sub-phthalocyanine derivative, fullerene or a fullerene derivative, thiophene or a thiophene derivative, or a combination thereof.

The fullerene may include C60, C70, C76, C78, C80, C82, C84, C90, C96, C240, C540, a mixture thereof, a fullerene nanotube, and the like. The fullerene derivative may refer to compounds of these fullerenes having a substituent thereof. The fullerene derivative may include a substituent such as an alkyl group (e.g., C1 to C30 alkyl group), an aryl group (e.g., C6 to C30 aryl group), a heterocyclic group (e.g., C3 to C30 cycloalkyl group), and the like. Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxazine ring, a phenoxathin ring, a phenothiazine ring, or a phenazine ring.

The sub-phthalocyanine or the sub-phthalocyanine derivative may be represented by Chemical Formula 7.

[Chemical Formula 7]

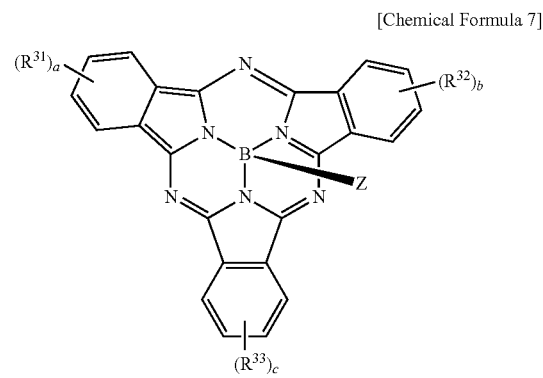

In Chemical Formula 7, $R^{31}$ to $R^{33}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a halogen-containing group, or a combination thereof, a, b, and c are integers of 1 to 3, and Z is a monovalent substituent.

For example, Z may be a halogen or a halogen-containing group, for example F, Cl, an F-containing group, or a Cl-containing group.

The halogen refers to F, Cl, Br, or I and the halogen-containing group refers to alkyl group (C1 to C30 alkyl group) where at least one of hydrogen is replaced by F, Cl, Br, or I.

The thiophene derivative may be for example represented by Chemical Formula 8 or 9, but is not limited thereto.

[Chemical Formula 8]

[Chemical Formula 9]

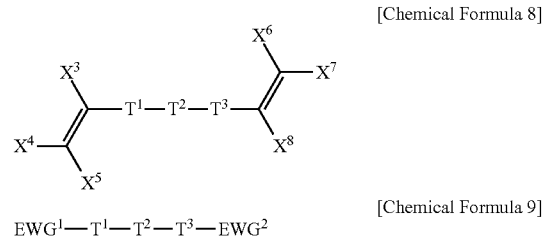

In Chemical Formula 8 and Chemical Formula 9, $T^1$, $T^2$, and $T^3$ are aromatic rings including substituted or unsubstituted thiophene moieties, $T^1$, $T^2$, and $T^3$ are independently present or are fused to each other, $X^3$ to $X^8$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a cyano group, or a combination thereof, and $EWG^1$ and $EWG^2$ are independently electron withdrawing groups.

For example, in Chemical Formula 8, at least one of $X^3$ to $X^8$ may be an electron withdrawing group, for example a cyano-containing group.

The active layer 30 may further include a second p-type semiconductor compound selectively absorbing green light. The second p-type semiconductor compound may be a compound represented by Chemical Formula 10.

[Chemical Formula 10]

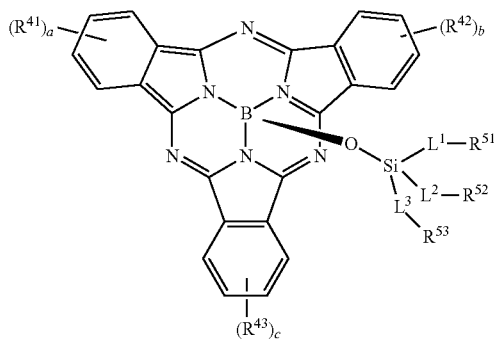

In Chemical Formula 10, $R^{41}$ to $R^{43}$ are independently hydrogen, a substituted or unsubstituted C1 to C30 aliphatic hydrocarbon group, a substituted or unsubstituted C6 to C30 aromatic hydrocarbon group, a substituted or unsubstituted C1 to C30 aliphatic heterocyclic group, a substituted or unsubstituted C2 to C30 aromatic heterocyclic group, a substituted or unsubstituted C1 to C30 alkoxy group, a substituted or unsubstituted C6 to C30 aryloxy group, a thiol group, a substituted or unsubstituted C1 to C30 alkylthio group, a substituted or unsubstituted C6 to C30 arylthio group, a cyano group, a cyano-containing group, a halogen, a halogen-containing group, a substituted or unsubstituted sulfonyl group (e.g., a substituted or unsubstituted C0 to C30 aminosulfonyl group, a substituted or unsubstituted C1 to C30 alkylsulfonyl group or a substituted or unsubstituted C6 to C30 arylsulfonyl group), or a combination thereof, or two adjacent groups of $R^{41}$ to $R^{43}$ are linked with each other to provide a fused ring, $L^1$ to $L^3$ are independently a single bond, a substituted or unsubstituted C1 to C30 alkylene group, a substituted or unsubstituted C6 to C30 arylene group, divalent a substituted or unsubstituted C3 to C30 heterocyclic group, or a combination thereof, $R^{51}$ to $R^{53}$ are independently a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group (e.g., a substituted or unsubstituted C1 to C30 alkylamine group or a substituted or unsubstituted C6 to C30 arylamine group), a substituted or unsubstituted silyl group, or a combination thereof, and a to c are independently integer of 0 to 4.

The second p-type semiconductor compound selectively absorbing green light may be included in an amount of about 500 to about 1500 parts by weight based on 100 parts by weight of the compound represented by Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the compound of Chemical Formula 1 and the n-type semiconductor compound in a ratio of about 1:100 to about 100:1. The compound of Chemical Formula 1 and the n-type semiconductor compound may be included in a ratio ranging from about 1:50 to about 50:1 within the range, specifically, about 1:10 to about 10:1, and more specifically, about 1:1. When the compound of Chemical Formula 1 and the n-type semiconductor compound have a composition ratio within the range, an exciton may be effectively produced, and a pn junction may be effectively formed.

The p-type layer may include the semiconductor compound of Chemical Formula 1, and the n-type layer may include the n-type semiconductor compound.

The active layer 30 may have a thickness of about 1 nm to about 500 nm and specifically, about 5 nm to about 300 nm. When the active layer 30 has a thickness within the range, the active layer may effectively absorb light, effectively separate holes from electrons, and deliver them, thereby effectively improving photoelectric conversion efficiency. A desirable thickness of the active layer 30 may be, for example, determined by an absorption coefficient of the active layer 30, and may be, for example, a thickness being capable of absorbing light of at least about 70% or more, for example about 80% or more, and for another example about 90%.

In the photoelectric device 100, when light enters from the first electrode 10 and/or second electrode 20, and when the active layer 30 absorbs light in a predetermined wavelength region, excitons may be produced from the inside. The excitons are separated into holes and electrons in the active layer 30, and the separated holes are transported to an anode that is one of the first electrode 10 and the second electrode 20 and the separated electrons are transported to the cathode that is the other of and the first electrode 10 and the second electrode 20 so as to flow a current in the photoelectric device.

Hereinafter, a photoelectric device according to another embodiment is described with reference to FIG. 2.

Figure 2:
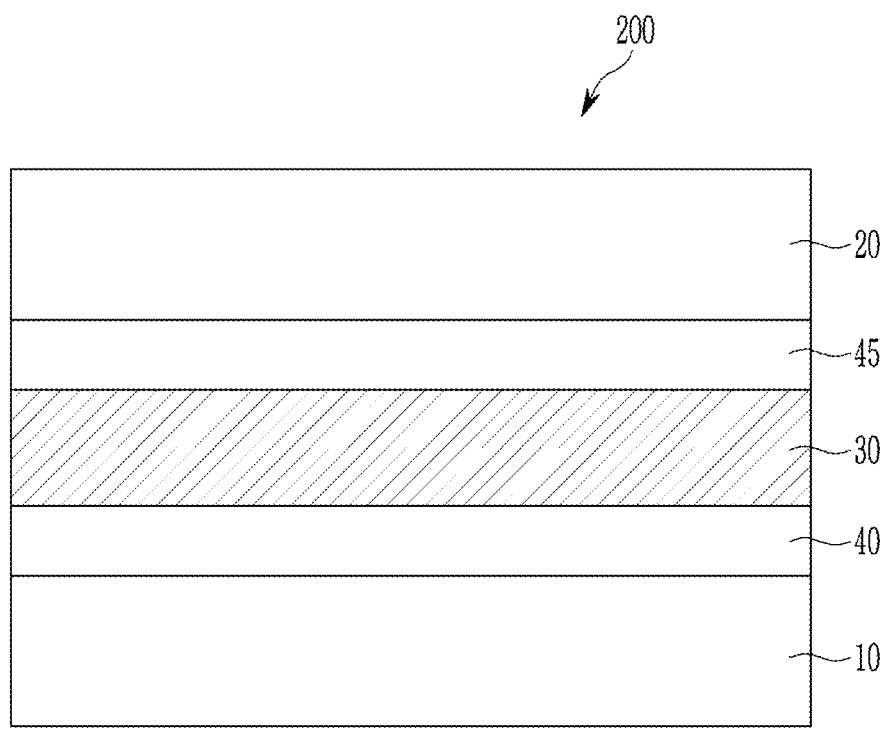
FIG. 2 is a cross-sectional view showing a photoelectric device according to another embodiment.

FIG. 2 is a cross-sectional view showing a photoelectric device according to another example embodiment.

Referring to FIG. 2, a photoelectric device 200 according to the present embodiment includes a first electrode 10 and a second electrode 20 facing each other, and an active layer 30 between the first electrode 10 and the second electrode 20, like the above embodiment.

However, the photoelectric device 200 according to the present embodiment further includes charge auxiliary layers 40 and 45 between the first electrode 10 and the active layer 30, and the second electrode 20 and the active layer 30, unlike the above embodiment. For example, the charge auxiliary layer 45 may be between the active layer 30 and the second electrode 20 and/or the charge auxiliary layer 40 may be between the active layer 30 and the first electrode 10. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for preventing electron transport, an electron injection layer (EIL) for facilitating electron injection, an electron transport layer (ETL) for facilitating electron transport, and a hole blocking layer (HBL) for preventing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include one selected from, for example, poly(3,4-ethylenedioxythiophene):poly (styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4''-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4''-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, Alq$_3$, Gaq$_3$, Inq$_2$, Znq$_2$, Zn(BTZ)$_2$, BeBq$_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, Alq$_3$, Gaq$_3$, Inq$_2$, Znq$_2$, Zn(BTZ)$_2$, BeBq$_2$, and a combination thereof, but is not limited thereto.

Either one of the charge auxiliary layers 40 and 45 may be omitted.

The photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
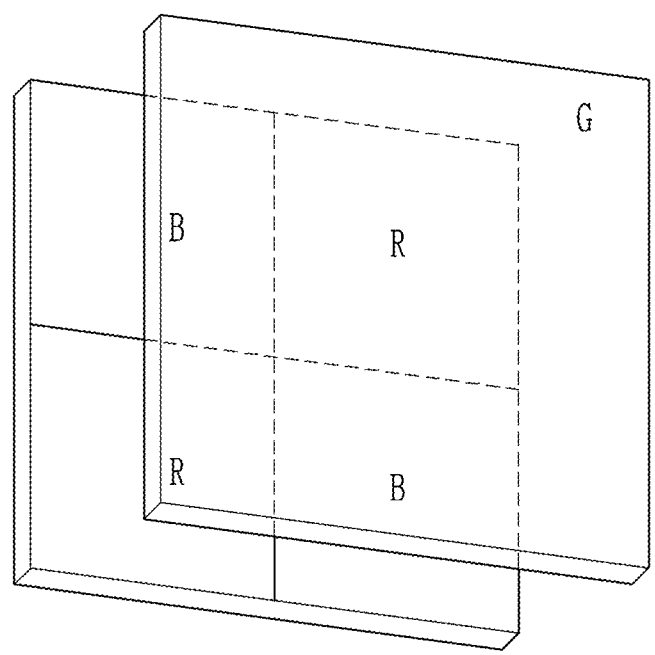
FIG. 3 is a schematic top plan view showing an organic CMOS image sensor according to an embodiment.
Figure 4:
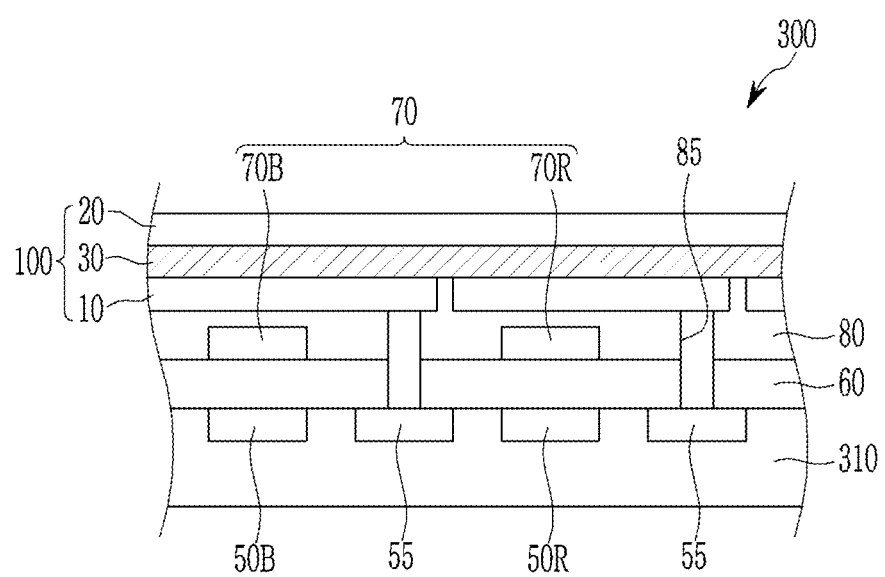
FIG. 4 is a cross-sectional view showing the organic CMOS image sensor of FIG. 3.

FIG. 3 is a schematic top plan view showing an organic CMOS image sensor according to an example embodiment, and FIG. 4 is a cross-sectional view showing the organic CMOS image sensor of FIG. 3.

Referring to FIGS. 3 and 4, an organic CMOS image sensor 300 according to an example embodiment includes a semiconductor substrate 310 integrated with photo-sensing devices 50B and 50R, a transmission transistor (not shown), a charge storage 55, a lower insulation layer 60, a color filter layer 70, an upper insulation layer 80, and a photoelectric device 100.

The semiconductor substrate 310 may be a silicon substrate, and is integrated with the photo-sensing devices 50B and 50R, the transmission transistor (not shown), and the charge storage 55. The photo-sensing devices 50R and 50B may be photodiodes.

The photo-sensing devices 50B and 50R, the transmission transistor, and/or the charge storage 55 may be integrated in each pixel, and as shown in the drawing, the photo-sensing devices 50B and 50R may be respectively included in a blue pixel and a red pixel and the charge storage 55 may be included in a green pixel.

The photo-sensing devices 50B and 50R sense light, the information sensed by the photo-sensing devices may be transferred by the transmission transistor, the charge storage 55 is electrically connected to the photoelectric device 100, and the information of the charge storage 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 310. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70B formed in the blue pixel and selectively transmitting blue light and a red filter 70R formed in the red pixel and selectively transmitting red light. In an embodiment, a cyan filter 70C and a yellow filter 70Y may be disposed instead of the blue filter 70B and red filter 70R. In the present embodiment, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The aforementioned photoelectric device 100 is formed on the upper insulation layer 80. The photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs and/or senses light in a green wavelength region and replaces a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

As described above, the photoelectric devices selectively absorbing light in a green wavelength region are stacked and thereby a size of an image sensor may be decreased and a down-sized image sensor may be realized.

As described above, the compound represented by the Chemical Formula 1 may be used as a semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

In an embodiment, in FIG. 4, additional color filters may be further disposed on the photoelectric device 100. The additional color filters may include a blue filter 70B and a red filter 70R or a cyan filter 70C and a yellow filter 70Y.

Figure 5:
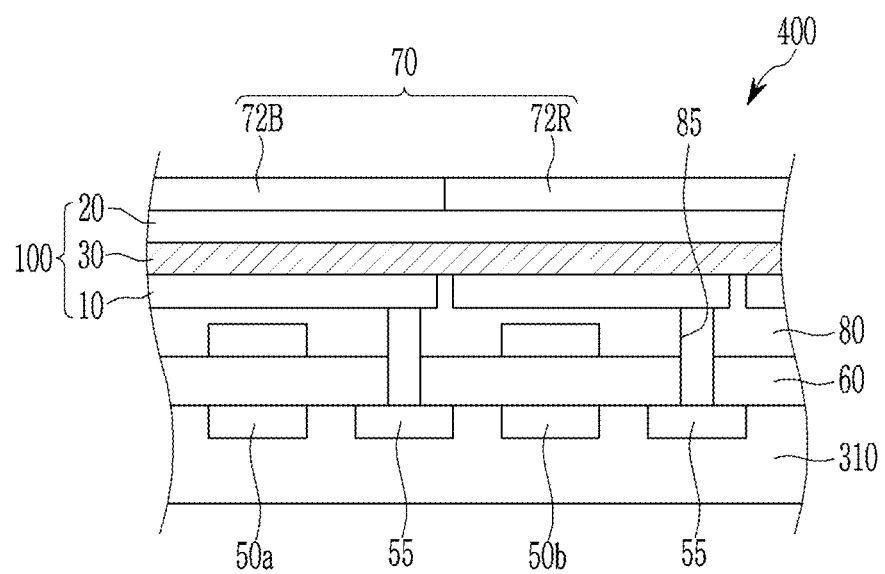
FIG. 5 is a schematic cross-sectional view showing an organic CMOS image sensor according to another embodiment.

The organic CMOS image sensor with the color filters disposed on the photoelectric device is shown in FIG. 5. FIG. 5 is a schematic cross-sectional view showing an organic CMOS image sensor according to an embodiment. Referring to FIG. 5, an organic CMOS image sensor 400 has the same structure as FIG. 4 except that a color filter layer 72 including the blue filter 72B and the red filter 72R is disposed on the photoelectric device 100. Instead of the blue filter 72B and the red filter 72R, the cyan filter 72C and the yellow filter 72Y may be disposed respectively.

Figure 6:
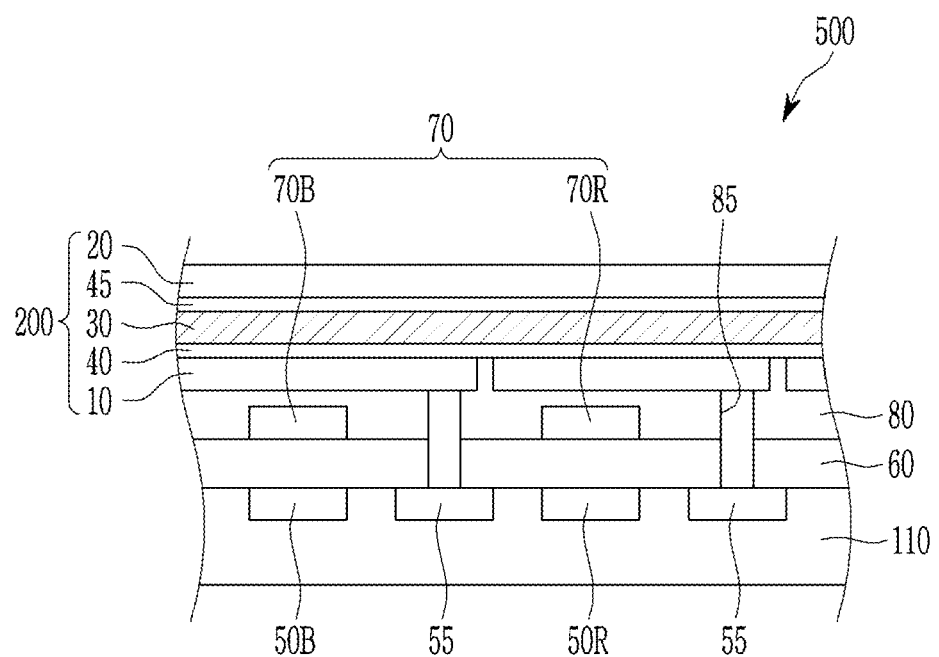
FIG. 6 is a schematic cross-sectional view showing an organic CMOS image sensor according to another embodiment.

In FIGS. 4 and 5, the photoelectric device 100 of FIG. 1 is included, but it is not limited thereto, and thus the photoelectric device 200 of FIG. 2 may be applied in the same manner. FIG. 6 is a cross-sectional view showing an organic CMOS image sensor 500 to which the photoelectric device 200 is applied.

Figure 7:
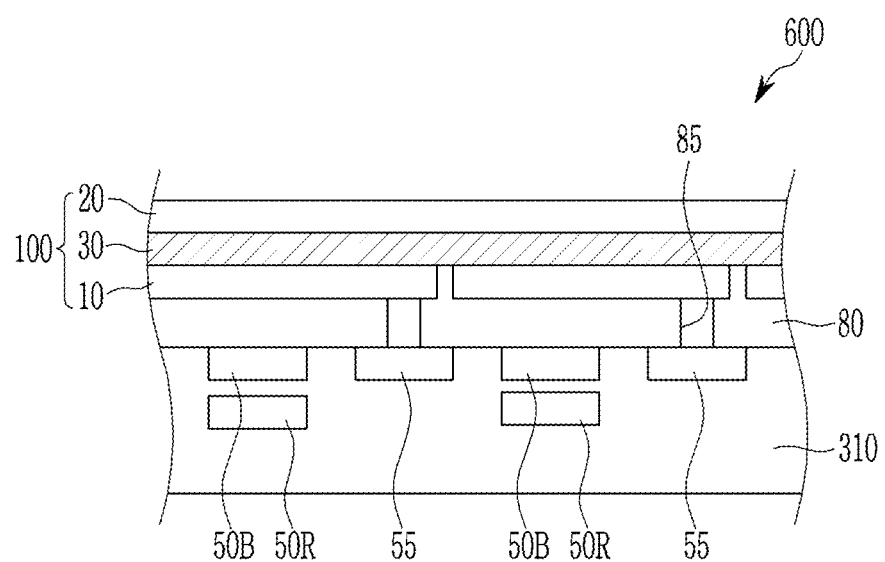
FIG. 7 is a schematic view showing an organic CMOS image sensor according to another embodiment.

FIG. 7 is a schematic view showing an organic CMOS image sensor according to another embodiment.

Referring to FIG. 7, the organic CMOS image sensor 600 includes a semiconductor substrate 310 integrated with photo-sensing devices 50B and 50R, a transmission transistor (not shown), a charge storage 55, an insulation layer 80, and a photoelectric device 100, like the example embodiment illustrated in FIG. 5.

However, the organic CMOS image sensor 600 according to the embodiment includes the blue photo-sensing device 50B and the red photo-sensing device 50R that are stacked and does not include a color filter layer 70, unlike the aforementioned embodiments. The blue photo-sensing device 50B and the red photo-sensing device 50R are electrically connected with the charge storage 55, and the information of the charge storage 55 may be transferred by the transmission transistor (not shown). The blue photo-sensing device 50B and the red photo-sensing device 50R may selectively absorb light in each wavelength region depending on a stack depth.

As described above, the photoelectric devices selectively absorbing light in a green wavelength region are stacked and the red photo-sensing device and the blue photo-sensing device are stacked, and thereby a size of an image sensor may be decreased and a down-sized image sensor may be realized. As described above, the photoelectric device 100 has improved green wavelength selectivity, and crosstalk caused by unnecessary absorption light in a wavelength region except green may be decreased while increasing sensitivity.

In FIG. 7, the photoelectric device 100 of FIG. 1 is included, but it is not limited thereto, and thus the photoelectric device 200 of FIG. 2 may be applied in the same manner.

Figure 8:
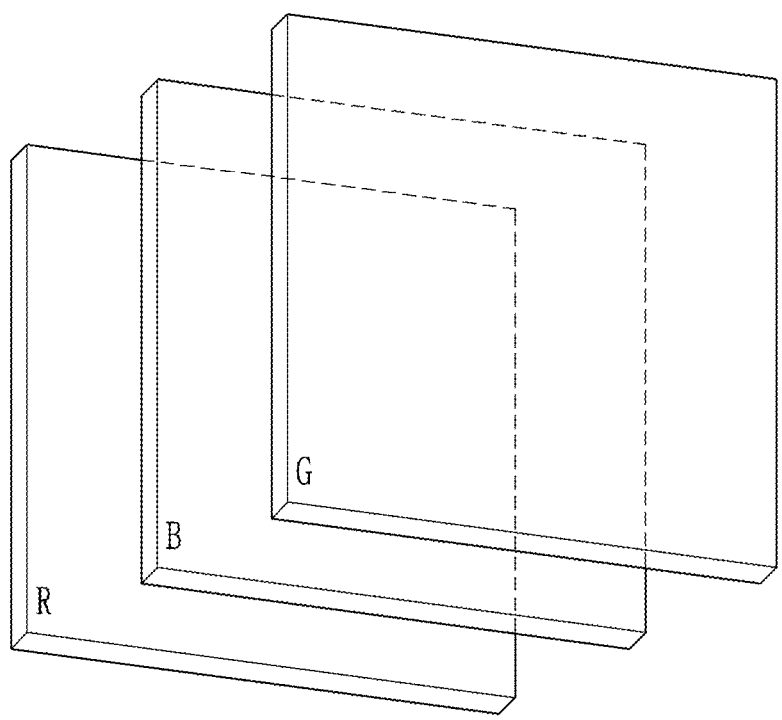
FIG. 8 is a schematic view showing an organic CMOS image sensor according to another embodiment.

FIG. 8 is a schematic view showing an organic CMOS image sensor according to another example embodiment.

Referring to FIG. 8, the organic CMOS image sensor according to the present embodiment includes a green photoelectric device (G) selectively absorbing light in a green wavelength region, a blue photoelectric device (B) selectively absorbing light in a blue wavelength region, and a red photoelectric device selectively absorbing light in a red wavelength region that are stacked.

In the drawing, the red photoelectric device, the green photoelectric device, and the blue photoelectric device are sequentially stacked, but the stack order may be changed without limitation.

The green photoelectric device may be the aforementioned photoelectric device 100 or photoelectric device 200, the blue photoelectric device may include electrodes facing each other and an active layer disposed therebetween and including an organic material selectively absorbing light in a blue wavelength region, and the red photoelectric device may include electrodes facing each other and an active layer disposed therebetween and including an organic material selectively absorbing light in a red wavelength region.

As described above, the green photoelectric device (G) selectively absorbing light in a green wavelength region, the blue photoelectric device (B) selectively absorbing light in a red wavelength region, and the red photoelectric device (R) selectively absorbing light in a blue wavelength region are stacked, and thereby a size of an image sensor may be decreased and a down-sized image sensor may be realized.

The image sensor absorbs light in an appropriate wavelength region and may show all improved sensitivity (YSNR10) and color reproducibility (ΔE*ab) despite a stacked structure.

Herein, the YSNR10 indicates sensitivity of the image sensor, which is measured in a method described in Juha Alakarhu's "Image Sensors and Image Quality in Mobile Phones" printed in 2007 International Image Sensor Workshop (Ogunquit Me., USA) but minimum illuminance expressed by lux at a ratio of 10 between signal and noise. Accordingly, the smaller the YSNR10 is, the higher sensitivity is.

On the other hand, the color reproducibility (ΔE*ab) shows a difference from standard colors in an X-Rite chart, and the ΔE*ab is defined as a distance between two points on a L*a*b* color space by CIE (Commission International de L'Eclairage) in 1976. For example, the color difference may be calculated according to Equation 1.

$$\Delta E = \sqrt{(\Delta L^*)^2 + (\Delta a^*)^2 + (\Delta b^*)^2}$$ [Equation 1]

In Equation 1,

ΔL* denotes a change of a color coordinate L* compared with the color coordinate rat room temperature (about 20° C. to about 25° C.), Δa* denotes a change of a color coordinate a* compared with the color coordinate a*at room temperature, and Δb* denotes a change of a color coordinate b* compared with the color coordinate b*at room temperature.

In order to produce an image sensor having high sensitivity and high color reproducibility, YSNR10≤100 lux at ΔE*ab≤3, and herein, the compound may realize YSNR10≤100 lux of sensitivity and color reproducibility at ΔE*ab≤3.

The image sensor may be applied to various electronic devices, for example, a mobile phone, a digital camera, and the like but is not limited thereto.

Figure 9:
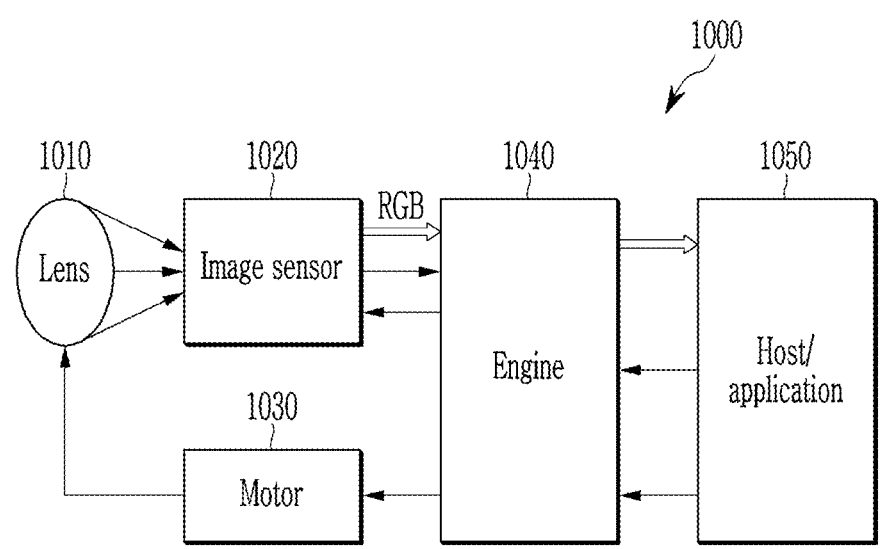
FIG. 9 is a block diagram of a digital camera including an image sensor according to an embodiment.

FIG. 9 is a block diagram of a digital camera including an image sensor according to an embodiment.

Referring to FIG. 9, a digital camera 1000 includes a lens 1010, an image sensor 1020, a motor unit 1030, and an engine unit 1040. The image sensor 1020 may be one of image sensors according to embodiments shown in FIGS. 3 to 8.

The lens 1010 concentrates incident light on the image sensor 1020. The image sensor 1020 generates RGB data for received light through the lens 1010.

In some embodiments, the image sensor 1020 may interface with the engine unit 1040.

The motor unit 1030 may adjust the focus of the lens 1010 or perform shuttering in response to a control signal received from the engine unit 1040. The engine unit 1040 may control the image sensor 1020 and the motor unit 1030.

The engine unit 1040 may be connected to a host/application 1050.

Hereinafter, the embodiments are illustrated in more detail with reference to examples. However, these examples are non-limiting, and the present disclosure is not limited thereto.

Synthesis Example 1: Synthesis of Compound Represented by Chemical Formula 1-1

[Chemical Formula 1-1]

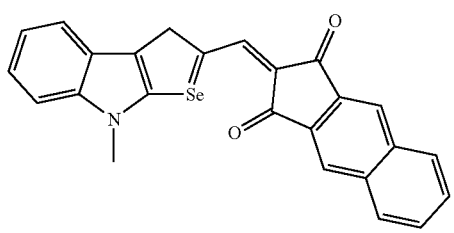

[Reaction Scheme 1-1]

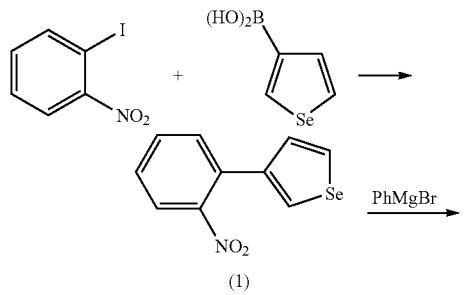

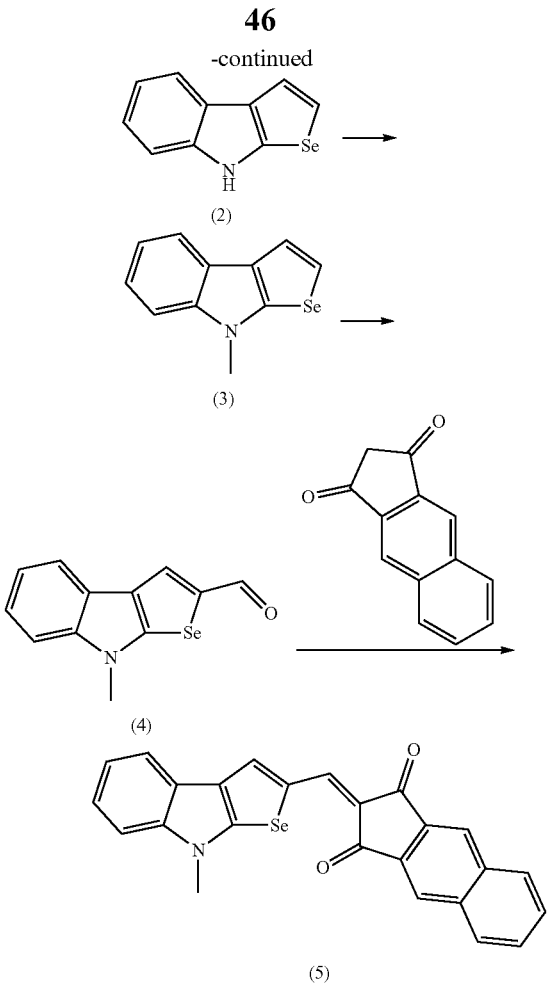

(i) Synthesis of Compound (1)

2.5 g (10.0 mmol) of 1-iodo-2-nitrobenzene, 2.28 g (13 mmol) of selenophene-3-yl boronic acid, and 0.58 g (0.5 mmol) of tetrakis(triphenylphosphine)palladium (0) are dissolved in 50 ml of dimethyl formamide (DMF) and 50 ml of water and then, reacted at 90° C. for 12 hours. A product obtained through extraction with diethyl ether at room temperature (24° C.) is separated and purified through silica gel column chromatography (a volume ratio of ethyl acetate:hexane=1:8) to obtain 2.2 g (Yield=87.3%) of Compound (1).

(ii) Synthesis of Compound (2)

5.0 g (19.8 mmol) of 3-(2-nitrophenyl)selenophene) is dissolved in 250 ml of dry THF and cooled down to 0° C., and then, 19.19 ml (59.5 mmol) of PhMgBr (1.0 M in a THF solution) are slowly added thereto in a dropwise fashion. While added over 10 minutes as above, a temperature of the solution is internally controlled not to be over 3° C. The solution is reacted at 0° C. for 5 minutes, and 50 ml of a NH$_4$Cl saturated solution is added thereto. 500 ml of water is added thereto, and an organic layer therefrom is washed with an aqueous sodium chloride solution, three times extracted with ethyl acetate, and dried with anhydrous magnesium sulfate. The obtained product is separated and purified through silica gel column chromatography (a volume ratio of ethyl acetate:hexane=1:5) to obtain 3.5 g (Yield=80.2%) of Compound (2), 8H-selenopheno[2,3-b]indole.

(iii) Synthesis of Compound (3)

3.0 g (13.6 mmol) of 8H-selenopheno[2,3-b]indole and 7.65 g (136.3 mmol) of potassium hydroxide are dissolved in 50 ml of dimethyl sulfoxide, and 13.2 g (40.9 mmol) of iodomethane is added thereto in a dropwise fashion. The obtained mixture is stirred at 30° C. for 5 hours. 250 ml of water is added thereto, and dichloromethane is used for an extraction. An extract therefrom is dried with anhydrous magnesium sulfate and then, separated and purified through silica gel column chromatography (a volume ratio of hexane:dichloromethane=5:1) to obtain 2.80 g (Yield=87.7%) of Compound (3), 8-methyl-8H-selenopheno[2,3-b]indole.

(iv) Synthesis of Compound (4)

2.4 ml of phosphoryl chloride is added to 15.0 ml of N,N-dimethylformamide in a dropwise fashion at −15° C. and then, stirred at room temperature (24° C.) for 2 hours. This is slowly added in a dropwise fashion to a mixture of 100 ml of dichloromethane and 1.3 g of Compound (3) at −15° C. and then, stirred at room temperature for 30 minutes and concentrated under a reduced pressure. Then, 150 ml of water is added thereto, and an aqueous sodium hydroxide solution is added thereto until pH becomes 14 and then, stirred at room temperature (24° C.) for 2 hours. An organic layer extracted with dichloromethane is washed with an aqueous sodium chloride solution and dried with anhydrous magnesium sulfate. A product therefrom is separated and purified through silica gel column chromatography (a volume ratio of hexane:ethyl acetate=4:1) to obtain 1.4 g (Yield=76.9%) of Compound (4), 8-methyl-8H-selenopheno[2,3-b]indole-2-carbaldehyde.

(iv) Synthesis of Compound (5)

0.75 g (2.86 mmol) of Compound (4) is suspended in ethanol, and 0.59 g (3.00 mmol) of 1H-cyclopenta[b]naphthalene-1,3(2H)-dione is added thereto and then, reacted at 50° C. for 2 hours to obtain 1.05 g (Yield=83.4%) of Compound (5). Compound (5) represented by Chemical Formula 1-1 is sublimed and purified up to purity of 99.9%.

$^1$H-NMR (500 MHz, Methylene Chloride-d$_2$): δ 8.8 (d, −2H), 8.3 (s, 1H), 8.2 (m, 2H), 8.0 (d, 1H), 7.8 (m, 2H), 7.5 (m, 2H), 7.2 (d, 1H), 6.7 (s, 1H), 3.7 (s, 3H).

Synthesis Example 2: Synthesis of Compound Represented by Chemical Formula 1-2

[Chemical Formula 1-2]

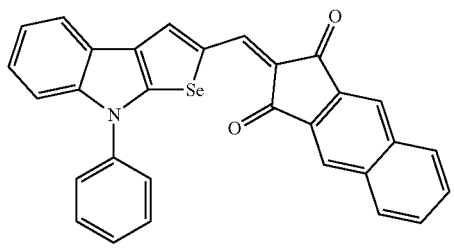

[Reaction Scheme 1-2]

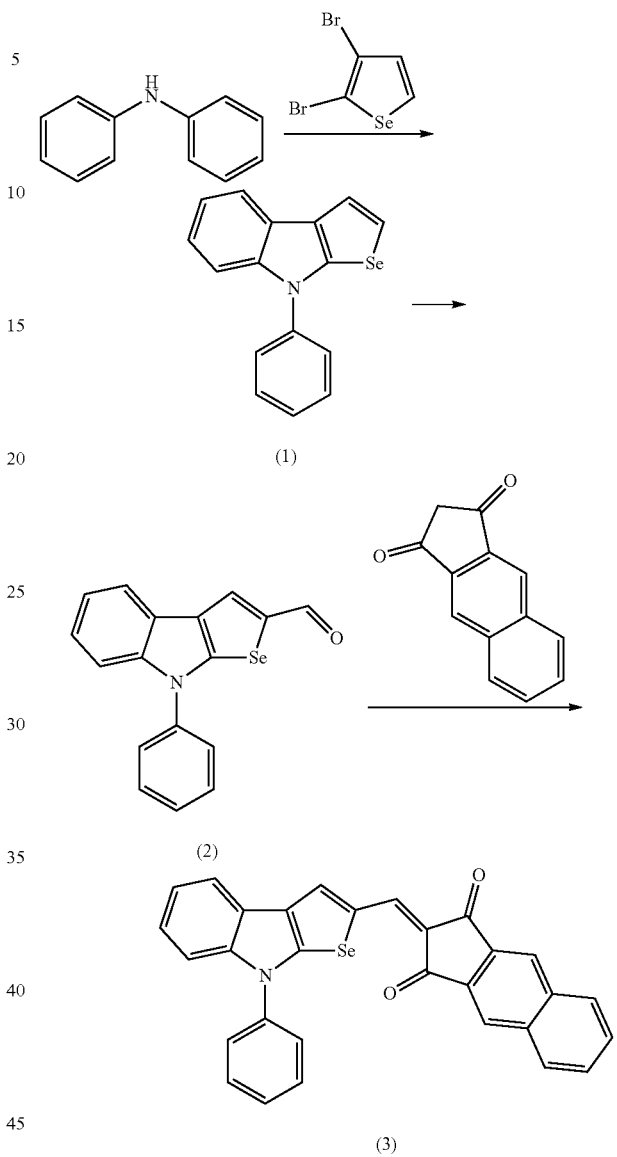

(i) Synthesis of Compound (1)

Diphenylamine (4.07 g, 24.0 mmol), palladium(II) acetate (135 mg, 0.6 mmol), tricyclohexylphosphine (336 mg, 1.2 mmol), sodium tert-butoxide (4.62 g, 48.0 mmol), and 2,3-dibromoselenophene (3.47 g, 12.0 mmol) are dissolved in 300 ml of toluene and then, reacted at 110° C. for 20 hours under a nitrogen environment. A product obtained through extraction with dichloromethane at room temperature is dried with MgSO$_4$ and separated and purified through silica gel column chromatography (a volume ratio of dichloromethane:hexane=1:9) to obtain 2.06 g (Yield=58%) of Compound (1).

(ii) Synthesis of Compound (2)

2.9 ml of phosphoryl chloride is added in a dropwise fashion to 18.0 ml of N,N-dimethylformamide at −15° C. and then, stirred at room temperature (24° C.) for 2 hours. The resultant is slowly added in a dropwise fashion to a mixture of 120 ml of dichloromethane and 2.0 g of Compound (1) at −15° C. and then, stirred at room temperature for 30 minutes and concentrated under a reduced pressure. Then, 200 ml of water is added thereto, and an aqueous sodium hydroxide solution is added thereto until pH becomes 14 and then, stirred for 2 hours at room temperature. An organic layer extracted with dichloromethane is washed with an aqueous sodium chloride solution and dried with anhydrous magnesium sulfate. A product therefrom is separated and purified through silica gel column chromatography (a volume ratio of hexane:ethyl acetate=4:1) to obtain 1.98 g (Yield=88.0%) of Compound (2), 8-phenyl-8H-selenopheno[2,3-b]indole-2-carbaldehyde.

(iii) Synthesis of Compound (3)

0.98 g (3.02 mmol) of Compound (2) is suspended in ethanol, and 0.65 g (3.32 mmol) of 1H-cyclopenta[b]naphthalene-1,3(2H)-dione is added thereto and reacted therewith at 50° C. for 2 hours to obtain 1.25 g (Yield=82.2%) of Compound (3). Compound (3) is sublimed and purified up to purity of 99.9%.

$^1$H-NMR (500 MHz, Methylene Chloride-d2): δ 8.8 (d, 2H), 8.3 (s, 1H), 8.4 (t, 1H), 8.2 (t, 2H), 7.8 (m, 2H), 7.6 (m, 6H), 7.3 (t, 2h), 6.7 (s, 1H).

Comparative Synthesis Example 1: Synthesis of Compound Represented by Chemical Formula 2-1

[Chemical Formula 2-1]

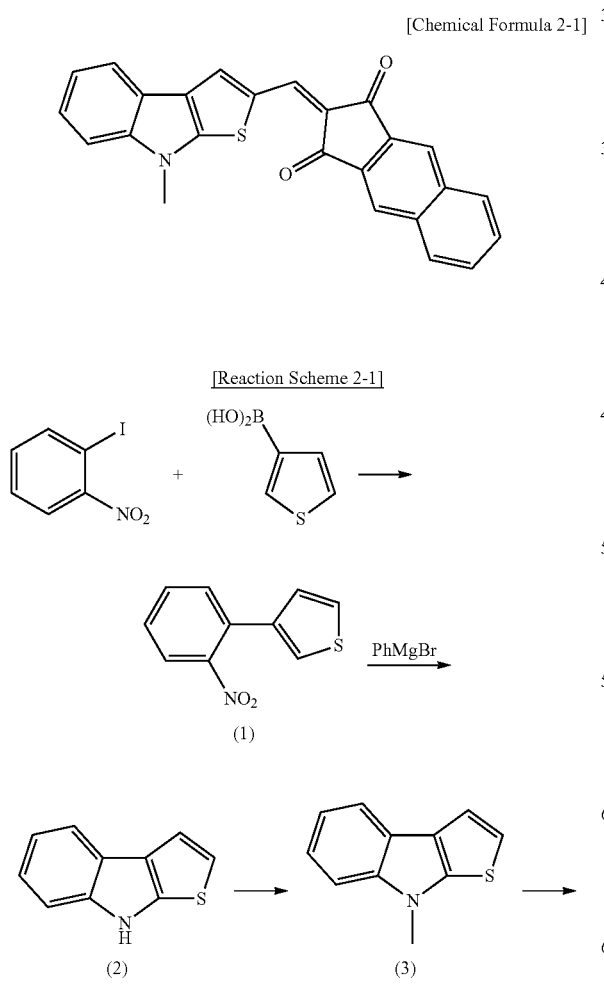

[Reaction Scheme 2-1]

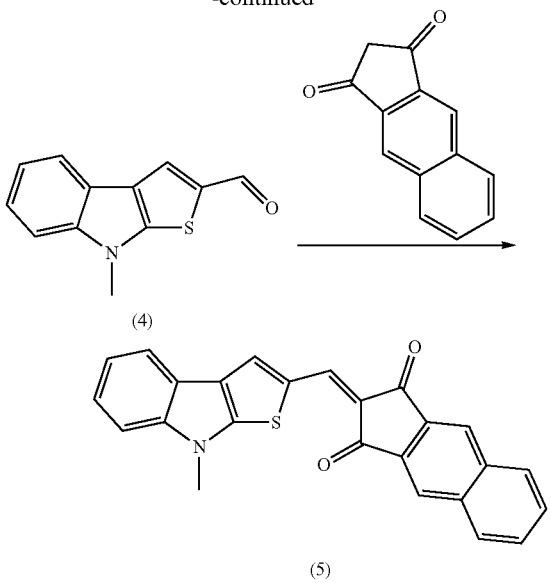

(i) Synthesis of Compound (1)

2.5 g (10.0 mmol) of 1-iodo-2-nitrobenzene, 1.67 g (13 mmol) of thiophene-3-yl boronic acid, and 0.58 g (0.5 mmol) of tetrakis(triphenylphosphine)palladium (0) are dissolved in 50 ml of DMF and 50 ml of water and then, reacted therewith at 90° C. for 12 hours. A product extracted with diethyl ether at room temperature is separated and purified through silica gel column chromatography (a volume ratio of ethyl acetate:hexane=1:8) to obtain 1.82 g (Yield=88.6%) of Compound (1).

(ii) Synthesis of Compound (2)

4.0 g (19.5 mmol) of 3-(2-nitrophenyl)thiophene) is dissolved in 250 ml of dry THF and cooled down to 0° C., and 18.9 ml (59.5 mmol) of PhMgBr (1.0 M in a THF solution is slowly added thereto in a dropwise fashion. While added over 10 minutes as above, a temperature of the solution is internally controlled not to be over 3° C. The solution is reacted at 0° C. for 5 minutes, and 50 ml of a NH$_4$Cl saturated solution is added thereto. 500 ml of water is added thereto, and an organic layer therefrom is washed with an aqueous sodium chloride solution, three times extracted with ethyl acetate, and dried with anhydrous magnesium sulfate. A product therefrom is separated and purified through silica gel column chromatography (a volume ratio of ethyl acetate:hexane=1:5) to obtain 2.88 g (Yield=85.2%) of Compound (2), 8H-thieno[2,3-b]indole.

(iii) Synthesis of Compound (3)

2.5 g (14.4 mmol) of 8H-thieno[2,3-b]indole and 8.10 g (144.3 mmol) of potassium hydroxide are dissolved in 50 ml of dimethyl sulfoxide, and 6.13 g (43.2 mmol) of iodomethane is added thereto in a dropwise fashion. The obtained mixture is stirred at 30° C. for 5 hours. 250 ml of water is added thereto, and dichloromethane is used for an extraction. An extract therefrom is dried with anhydrous magnesium sulfate, separated and purified through silica gel column chromatography (a volume ratio of hexane:dichloromethane=5:1) to obtain 2.29 g (Yield=85.2%) of Compound (3), 8-methyl-8H-thieno[2,3-b]indole.

(iv) Synthesis of Compound (4)

2.4 ml of phosphoryl chloride is added in a dropwise fashion to 15.0 ml of N,N-dimethylformamide at −15° C. and then, stirred at room temperature for 2 hours. This is slowly added in a dropwise fashion to a mixture of 100 ml of dichloromethane and 1.0 g of Compound (3) at −15° C. and then, stirred at room temperature for 30 minutes and concentrated under a reduced pressure. Then, 150 ml of water is added thereto, and an aqueous sodium hydroxide solution is added thereto until pH becomes 14 and then, stirred at room temperature (24° C.) for 2 hours. An organic layer extracted with dichloromethane is washed with an aqueous sodium chloride solution and then, dried with anhydrous magnesium sulfate. A product therefrom is separated and purified through silica gel column chromatography (a volume ratio of hexane:ethyl acetate=4:1) to obtain 1.12 g (Yield=98.0%) of Compound (4), 8-methyl-8H-selenopheno[2,3-b]indole-2-carbaldehyde.

(iv) Synthesis of Compound (5)

0.7 g (3.25 mmol) of Compound (4) is suspended in ethanol, and 0.70 g (3.58 mmol) of 1H-cyclopenta[b]naphthalene-1,3(2H)-dione is added thereto and reacted therewith at 50° C. for 2 hours to obtain 1.08 g (Yield=84.7%) of Compound (5). Compound (5) represented by Chemical Formula 2-1 is sublimed and purified up to purity of 99.9%.

$^1$H-NMR (500 MHz, Methylene Chloride-d2): δ 8.8 (d, 2H), 8.5 (s, 1H), 8.2 (m, 2H), 8.1 (d, 1H), 7.9 (s, 1H), 7.8 (m, 2H), 7.6 (d, 1H), 7.3 (m, 2H), 3.7 (s, 3H).

Comparative Synthesis Example 2: Synthesis of Compound Represented by Chemical Formula 2-2

[Chemical Formula 2-2]

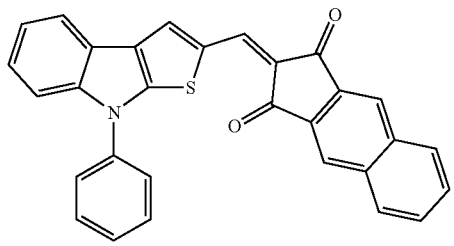

[Reaction Scheme 2-2]

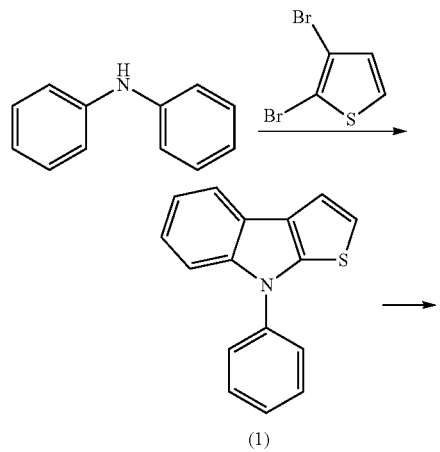

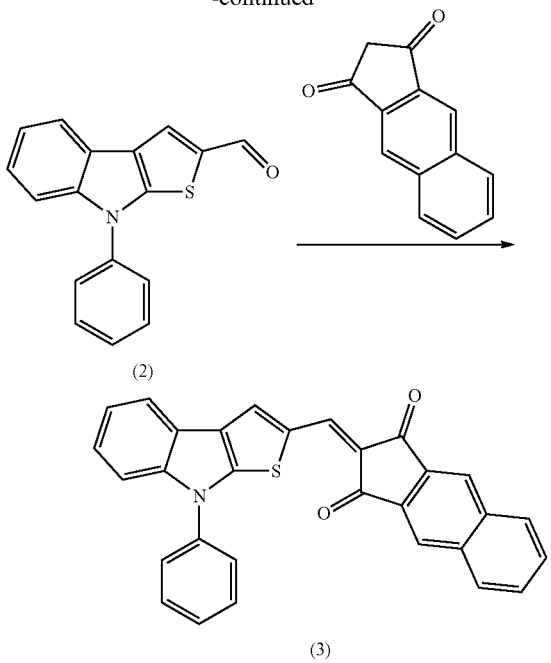

(i) Synthesis of Compound (1)

Diphenylamine (4.07 g, 24.0 mmol), palladium(II) acetate (135 mg, 0.6 mmol), tricyclohexylphosphine (336 mg, 1.2 mmol), sodium tert-butoxide (4.62 g, 48.0 mmol), and 2,3-dibromothiophene (2.90 g, 12.0 mmol) are dissolved in 300 ml of toluene and reacted at 110° C. for 20 hours under a nitrogen environment. A product extracted with dichloromethane at room temperature is dried with MgSO$_4$ and separated and purified through silica gel column chromatography (a volume ratio of dichloromethane:hexane=1:9) to obtain 1.86 g (Yield=62%) of Compound (1).

(ii) Synthesis of Compound (2)

2.5 ml of phosphoryl chloride is added in a dropwise fashion to 15.0 ml of N,N-dimethylformamide at −15° C. and then, stirred at room temperature (24° C.) for 2 hours. This is slowly added in a dropwise fashion to a mixture of 100 ml of dichloromethane and 1.8 g of Compound (1) at −15° C. and then, stirred at room temperature for 30 minutes and concentrated under a reduced pressure. Then, 150 ml of water is added thereto, and an aqueous sodium hydroxide solution is added thereto until pH becomes 14 and then, stirred at room temperature (24° C.) for 2 hours. An organic layer extracted with dichloromethane is washed with an aqueous sodium chloride solution and dried with anhydrous magnesium sulfate. The obtained product is separated and purified through silica gel column chromatography (a volume ratio of hexane:ethyl acetate=4:1) to obtain 1.80 g (Yield=90.0%) of Compound (2), 8-phenyl-8H-thieno[2,3-b]indole-2-carbaldehyde.

(iii) Synthesis of Compound (3)

1.00 g (3.61 mmol) of Compound (2) is suspended in ethanol, and 0.78 g (3.97 mmol) of 1H-cyclopenta[b]naphthalene-1,3(2H)-dione is added thereto and then, reacted therewith at 50° C. for 2 hours to obtain 1.40 g (Yield=85.2%) of Compound (3). Compound (3) represented by Chemical Formula 2-2 is sublimed and purified up to purity of 99.9%.

¹H-NMR (500 MHz, Methylene Chloride-d₂): δ 8.8 (d, 2H), 8.5 (s, 1H), 8.6 (t, 1H), 8.2 (t, 2H), 7.9 (m, 2H), 7.8 (m, 2H), 7.6 (m, 5H), 7.4 (t, 1h), 7.2 (t, 1H)

Example 1: Production of Photoelectric Device

An about 150 nm-thick anode is formed by sputtering ITO on a glass substrate, and a 100 nm-thick active layer is formed thereon by codepositing a compound represented by Chemical Formula 1-1 according to Synthesis Example 1 (a p-type semiconductor compound) and C60 (an n-type semiconductor compound) in a volume ratio of 1:1. Subsequently, a 10 nm-thick molybdenum oxide ($MoO_x$, $0<x\leq3$) thin film is formed thereon as a charge auxiliary layer. On the molybdenum oxide thin film, a 7 nm-thick cathode is formed by sputtering ITO, manufacturing an organic photoelectric device.

Example 2, Comparative Example 1 and Comparative Example 2: Production of Photoelectric Device Photoelectric devices according to Example 2, Comparative Example 1, and Comparative Example 2 are produced according to the same method as Example 1 except that the compounds according to Synthesis Example 2, Comparative Synthesis Example 1, and Comparative Synthesis Example 2 are used respectively instead of the compound according to Synthesis Example 1.

Evaluation 1: Light Absorption Characteristics of Synthesis of Compounds

Light absorption characteristics depending on a wavelength (a maximum absorption wavelength and a full width at half maximum (FWHM)) of the compounds according to Synthesis Examples 1 and 2 and Comparative Synthesis Example 2 are evaluated. Each compound (a p-type semiconductor compound) according to Synthesis Examples 1 and 2 and Comparative Synthesis Example 2 and C60 (an n-type semiconductor compound) are codeposited in a volume ratio of 1:1 to form 100 nm-thick thin films, and the light absorption characteristics of each thin film in a ultraviolet (UV)-visible ray (UV-Vis) region are evaluated by using Cary 5000 UV spectroscopy (Varian Inc.).

TABLE 1

| Compounds | $\lambda_{max}$ (nm) | FWHM (nm) |
|---|---|---|
| Synthesis Example 1 | 520 | 150 |
| Synthesis Example 2 | 510 | 150 |
| Comparative Synthesis Example 2 | 490 | 175 |

Referring to Table 1, the compounds of Synthesis Examples 1 and 2 exhibit a maximum absorption wavelength ($\lambda_{max}$) and a low full width at half maximum (FWHM) at greater than or equal to 510 nm. Accordingly, the compounds according to Synthesis Examples 1 and 2 have high wavelength selectivity in the green wavelength region. On the contrary, the compound of Comparative Synthesis Example 2 exhibits a maximum absorption wavelength and a full width at half maximum (FWHM) out of the green wavelength region.

Evaluation 2: Energy Level and Bandgap of Compounds

The compounds of Synthesis Examples 1 and 2 are measured with respect to HOMO energy levels by using an AC-3 photoelectron spectrophotometer (RIKEN KEIKI), and bandgaps thereof are measured with Cary 5000 UV spectroscopy (Varian Inc.) and respectively used to calculate LUMO energy levels. The results are shown in Table 2.

TABLE 2

| Compounds | HOMO (eV) | LUMO (eV) | Bandgap (eV) |
|---|---|---|---|
| Synthesis Example 1 | −6.03 | −3.11 | −2.92 |
| Synthesis Example 2 | −5.95 | −3.13 | −2.82 |

Referring to Table 2, the compounds of Synthesis Examples 1 and 2 are respectively applied as a p-type semiconductor compound.

Evaluation 3: Aspect Ratio of Compounds

The compounds of Synthesis Examples 1 and 2 are respectively calculated with respect to a molecular skeleton of an energetically-optimized structure through Density Functional Theory (DFT), and in the corresponding skeleton, a ratio (z/x) of the shortest length (z) relative to the longest length (x) is calculated to obtain an aspect ratio. The results are shown in Table 3.

TABLE 3

| Compounds | Aspect ratio (z/x) |
|---|---|
| Synthesis Example 1 | 0.213 |
| Synthesis Example 2 | 0.304 |

Referring to Table 3, the compounds of Synthesis Examples 1 and 2 have a low aspect ratio and thus maintain a planarity.

Evaluation 4: Thermal Stability of Compounds

In order to evaluate thermal stability of the compounds according to Synthesis Examples 1 and 2, a temperature ($Ts_{10}$, a deposition temperature) where 10 wt % thereof is sublimated at 10 Pa, and a temperature ($Ts_{50}$, a deposition temperature) where 50 wt % is sublimated at 10 Pa are measured. The deposition temperatures are measured in a thermal gravimetric analysis (TGA) method while increasing the temperature from room temperature to 500° C. The results are shown in Table 4.

TABLE 4

| | Tm (° C.) | $Ts_{10}$ (10 wt %, 10 Pa) (° C.) | $Ts_{50}$ (50 wt %, 10 Pa) (° C.) | ΔT (Tm − Ts) (° C.) |
|---|---|---|---|---|
| Synthesis Example 1 | 306 | 250 | 280 | 30 |
| Synthesis Example 2 | 325 | 262 | 298 | 36 |

When a compound has a lower melting point than a deposition temperature during the vacuum deposition, the compound may be decomposed and simultaneously gasified and thus fails in being formed into a film. Accordingly, the melting point of a compound may desirably be higher than the deposition temperature. Referring to Table 4, the compounds of Synthesis Examples 1 and 2 exhibit a higher melting point than the deposition temperature by greater than or equal to 30° C. Accordingly, the compounds of Synthesis Examples 1 and 2 all exhibit a large difference between melting point and deposition temperature and thus may advantageously secure process stability.

Evaluation 5: Charge Mobility of Photoelectric Device

In order to evaluate charge mobility of a photoelectric device, TOF mobility is measured. TOF mobility of the photoelectric devices according to Examples 1 and 2 and Comparative Example 2 is evaluated by using PTI (Photon Technology International GL-3300, an N₂ laser, 337 nm) as a light source and a storage oscilloscope (1 GHz). The results are shown in Table 5.

TABLE 5

| Photoelectric device | TOF mobility (cm²/V · sec) |
|---|---|
| Example 1 | $7.2 \times 10^{-4}$ |
| Example 2 | $2.4 \times 10^{-4}$ |
| Comparative Example 2 | $2.0 \times 10^{-4}$ |

Referring to Table 5, the photoelectric devices of Examples 1 and 2 respectively using the compounds of Synthesis Examples 1 and 2 exhibit excellent mobility compared with the photoelectric device of Comparative Example 2 including the compound of Comparative Synthesis Example 2.

Evaluation 6: External Quantum Efficiency of Photoelectric Device

External quantum efficiency (EQE) of the photoelectric devices according to Examples 1 and 2 and Comparative Examples 1 and 2 is evaluated. The external quantum efficiency is measured by using an IPCE measurement system (McScience Inc., Korea). First, an Si photodiode (Hamamatsu Photonics K.K., Japan) is used to calibrate the system, and the photoelectric devices according to Examples 1 and 2 and Comparative Examples 1 and 2 are mounted on the system, and then, the external quantum efficiency thereof is measured in a wavelength range of about 350 nm to 750 nm.

In addition, the photoelectric devices of Examples 1 and 2 and Comparative Examples 1 and 2 are respectively heat-treated at 160° C. for 3 hours and at 170° C. for 3 hours and then, measured with respect to external quantum efficiency in a wavelength range of about 350 nm to about 750 nm by using the equipment.

The results of Examples 1 and 2 and Comparative Example 2 are shown in Table 6. In Table 6, the external quantum efficiency is obtained at a maximum absorption wavelength when a voltage of −3 V is applied.

TABLE 6

| Device | EQE (%) at −3 V | | |
|---|---|---|---|
| | No heat treatment | 160° C. (3 h) | 170° C. (3 h) |
| Example 1 | 56 | 56 | 57 |
| Example 2 | 42 | 42 | 40 |
| Comparative Example 2 | 35 | 32 | 24 |

Referring to Table 6, the photoelectric devices of Examples 1 and 2 exhibit excellent external quantum efficiency after a high temperature heat treatment as well as room temperature (no heat treatment) compared with the photoelectric device of Comparative Example 2.

Evaluation 8: Response Time of Photoelectric Device

Response time (lag time) of the photoelectric devices according to Examples 1 and 2 and Comparative Examples 1 and 2 is evaluated. The response time is evaluated by heat-treating the photoelectric devices of Examples 1 and 2 and Comparative Examples 1 and 2 at 170° C. for 3 hours, radiating LED light at a central wavelength of 530 nm from an upper electrode (a cathode) into the photoelectric devices, applying an electric field of 3 V/100 nm to the photoelectric devices, turning off the LED light, and 0.1 second later, measuring after-image currents thereof.

The results of Example 1 and Comparative Examples 1 and 2 are shown in Table 7.

TABLE 7

| | Lag time @ 10 μW/cm² (ms) |
|---|---|
| Example 1 | 280 |
| Comparative Example 1 | 464 |
| Comparative Example 2 | 579 |

Referring to Table 7, the photoelectric device of Example 1 exhibits fast response time after the high temperature heat treatment compared with the photoelectric devices of Comparative Examples 1 and 2.

While this disclosure has been described in connection with what is presently considered to be practical example embodiments, it is to be understood that the inventive concepts are not limited to the disclosed embodiments. On the contrary, it is intended to cover various modifications and equivalent arrangements included within the spirit and scope of the appended claims.

<Description of Symbols>

| 10: first electrode | 20: second electrode |
|---|---|
| 30: active layer | 40, 45: charge auxiliary layer |
| 100, 200: photoelectric device | 300, 400, 500, 600: organic CMOS image sensor |
| 310: semiconductor substrate | 70B, 72B: blue filter |
| 70R, 72R: red filter | |
| 70, 72: color filter layer | 85: through-hole |
| 60: lower insulation layer | 80: upper insulation layer |
| 50B, 50R: photo-sensing device | 55: charge storage |

What is claimed is:

1. A compound represented by Chemical Formula 1:

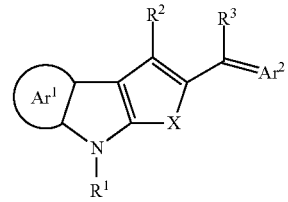

[Chemical Formula 1]

wherein, in Chemical Formula 1

Ar¹ is a substituted or unsubstituted C6 to C30 arene group or a substituted or unsubstituted C3 to C30 heteroarene group, Ar² is a substituted or unsubstituted C6 to C30 hydrocarbon cyclic group, a substituted or unsubstituted C6 to C30 heterocyclic group, or a fused ring thereof, Ar² has at least one functional group selected from C=O, C=S, C=Se, and C=Te X is Se, Te, SiRᵃRᵇ, or GeRᶜRᵈ (wherein Rᵃ, Rᵇ, Rᶜ, and Rᵈ are independently hydrogen, deuterium, or a substituted or unsubstituted C1 to C10 alkyl group, and wherein Rᵃ, Rᵇ, Rᶜ, and Rᵈ are independently present or Rᵃ and Rᵇ or Rᶜ and Rᵈ are linked with each other to provide a spiro structure), and R¹ to R³ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiR$^a$R$^b$R$^c$ (wherein R$^a$, R$^b$, and Re are independently hydrogen or a substituted or unsubstituted C1 to C10 alkyl group), or a combination thereof.

2. The compound of claim 1, wherein in Chemical Formula 1, R$^1$ is a substituted or unsubstituted C1 to C30 alkyl group or a substituted or unsubstituted C6 to C30 aryl group.

3. The compound of claim 1, wherein in Chemical Formula 1, Ar$^1$ is a substituted or unsubstituted benzene, a substituted or unsubstituted naphthalene, a substituted or unsubstituted indene, a substituted or unsubstituted anthracene, a substituted or unsubstituted phenanthrene, a substituted or unsubstituted fluorine, or a substituted or unsubstituted acenaphthylene.

4. The compound of claim 1, A compound represented by Chemical Formula 1:
wherein, in Chemical Formula 1, Ar$^1$ is a substituted or unsubstituted pyridine, a substituted or unsubstituted pyrimidine, a substituted or unsubstituted pyrazine, a substituted or unsubstituted indole, a substituted or unsubstituted quinoline, a substituted or unsubstituted isoquinoline, a substituted or unsubstituted quinoxaline, a substituted or unsubstituted quinazoline, a substituted or unsubstituted carbazole, a substituted or unsubstituted phenazine, or a substituted or unsubstituted phenanthroline.

5. The compound of claim 1, wherein in Chemical Formula 1, X is one of Se and Te.

6. The compound of claim 1, wherein Are is a cyclic group represented by Chemical Formula 3:

[Chemical Formula 3]

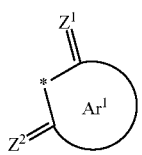

wherein, in Chemical Formula 3,
Ar$^1$ is a substituted or unsubstituted C6 to C30 aryl group or a substituted or unsubstituted C3 to C30 heteroaryl group,
Z$^1$ is O, S, Se, or Te, and
Z$^2$ is O, S, Se, Te, or CR$^a$R$^b$, wherein R$^a$ and R$^b$ are independently hydrogen, a substituted or unsubstituted C1 to C10 alkyl group, a cyano group, or a cyano-containing group, provided that when Z$^2$ is CR$^a$R$^b$, at least one of R$^a$ and R$^b$ is a cyano group or a cyano-containing group.

7. The compound of claim 1, wherein in Chemical Formula 1, Are is a cyclic group represented by one of Chemical Formula 4A to Chemical Formula 4F:

[Chemical Formula 4A]

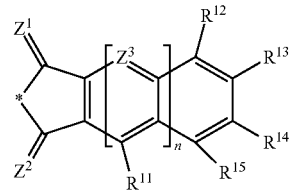

wherein, in Chemical Formula 4A,
Z$^1$ is O, S, Se, or Te,
Z$^2$ is O, S, Se, Te, or CR$^a$R$^b$, wherein R$^a$ and R$^b$ are independently hydrogen, a substituted or unsubstituted C1 to C10 alkyl group, a cyano group, or a cyano-containing group, provided that when Z$^2$ is CR$^a$R$^b$, at least one of R$^a$ and R$^b$ is a cyano group or a cyano-containing group,
Z$^3$ is N or CR$^c$ (wherein R$^c$ is hydrogen, deuterium, or a substituted or unsubstituted C1 to C10 alkyl group),
R$^{11}$, R$^{12}$, R$^{13}$, R$^{14}$, and R$^{15}$ are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, wherein R$^{11}$, R$^{12}$, R$^{13}$, R$^{14}$, and R$^{15}$ are independently present or at least one of R$^{12}$ and R$^{13}$ and R$^{14}$ and R$^{15}$ is linked with each other to provide a fused aromatic ring,
n is 0 or 1, and
* is a linking position,

[Chemical Formula 4B]

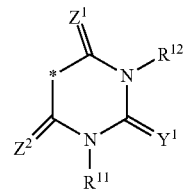

wherein, in Chemical Formula 4B,
Z$^1$ is O, S, Se, or Te,
Z$^2$ is O, S, Se, Te, or CR$^a$R$^b$, wherein R$^a$ and R$^b$ are independently hydrogen, a substituted or unsubstituted C1 to C10 alkyl group, a cyano group, or a cyano-containing group, provided that when Z$^2$ is CR$^a$R$^b$, at least one of R$^a$ and R$^b$ is a cyano group or a cyano-containing group,
Y$^1$ is O, S, Se, Te, or C(R$^a$)(CN) (wherein R$^a$ is hydrogen, a cyano group (—CN), or a C1 to C10 alkyl group),
R$^{11}$ and R$^{12}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and
* is a linking position,

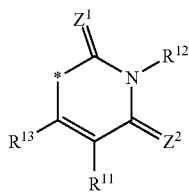

[Chemical Formula 4C]

wherein, in Chemical Formula 4C, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $R^{11}$, $R^{12}$, and $R^{13}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, and

* is a linking position,

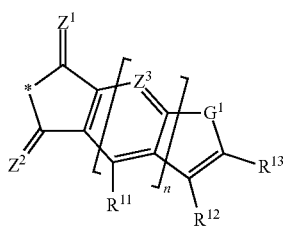

[Chemical Formula 4D]

wherein, in Chemical Formula 4D, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Z^3$ is N or $CR^c$ (wherein $R^c$ is hydrogen or a substituted or unsubstituted C1 to C10 alkyl group), $G^1$ is O, S, Se, Te, $SiR^xR^y$, or $GeR^zR^w$, wherein $R^x$, $R^y$, $R^z$, and $R^w$ are independently hydrogen, a halogen, a substituted or unsubstituted C1 to C10 alkyl group, or a substituted or unsubstituted C6 to C10 aryl group, $R^{11}$, $R^{12}$, and $R^{13}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, wherein $R^{12}$ and $R^{13}$ are independently different and are linked with each other to provide a fused aromatic ring, n is 0 or 1, and

* is a linking position,

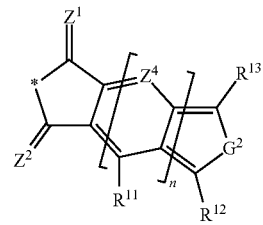

[Chemical Formula 4E]

wherein, in Chemical Formula 4E, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $G^2$ is O, S, Se, Te, $SiR^xR^y$, or $GeR^zR^w$, wherein $R^x$, $R^y$, $R^z$, and $R^w$ are independently hydrogen, a halogen, a substituted or unsubstituted C1 to C10 alkyl group, or a substituted or unsubstituted C6 to C10 aryl group, $R^{11}$, $R^{12}$, and $R^{13}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, and

* is a linking position,

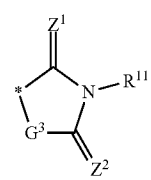

[Chemical Formula 4F]

wherein, in Chemical Formula 4F, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $R^{11}$ is hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^3$ is O, S, Se, Te, $SiR^xR^y$, or $GeR^zR^w$, wherein $R^x$, $R^y$, $R^z$, and $R^w$ are independently hydrogen, a halogen, a substituted or unsubstituted C1 to C10 alkyl group, or a substituted or unsubstituted C6 to C10 aryl group.

8. The compound of claim 1, wherein the compound of Chemical Formula 1 is a compound represented by Chemical Formula 5A or 5B:

[Chemical Formula 5A]

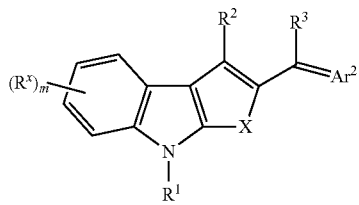

wherein, in Chemical Formula 5A,
Ar$^2$, X, and R$^1$ to R$^3$ are the same as in Chemical Formula 1,
R$^x$ is hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ are independently hydrogen or a substituted or unsubstituted C1 to C10 alkyl group), or a combination thereof, and
m is an integer of 1 to 4,

[Chemical Formula 5B]

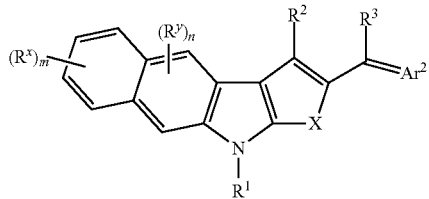

wherein, in Chemical Formula 5B,
Ar$^2$, X, and R$^1$ to R$^3$ are the same as in Chemical Formula 1,
R$^x$ and R$^y$ are hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ are independently hydrogen or a substituted or unsubstituted C1 to C10 alkyl group), or a combination thereof,
m is an integer of 1 to 4, and
n is an integer of 1 or 2.

9. The compound of claim 1, wherein the compound of Chemical Formula 1 is a compound represented by Chemical Formula 5C or 5D:

[Chemical Formula 5C]

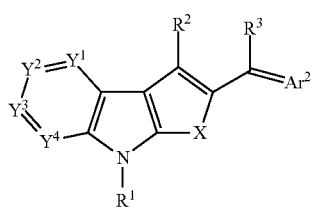

wherein, in Chemical Formula 5C,
Ar$^2$, X, and R$^1$ to R$^3$ are the same as in Chemical Formula 1, and
Y$^1$ to Y$^4$ are independently CR$^x$R$^y$ or NR$^z$ (wherein R$^x$, R$^y$, and R$^z$ are hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiR$^a$R$^b$R$^c$ (wherein R$^a$, R$^b$, and Re are independently hydrogen or a substituted or unsubstituted C1 to C10 alkyl group), or a combination thereof, provided that at least one of Y$^1$ to Y$^4$ is NR$^z$,

[Chemical Formula 5D]

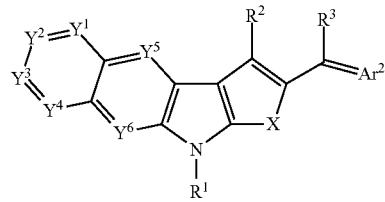

wherein, in Chemical Formula 5D,
Ar$^2$, X, and R$^1$ to R$^3$ are the same as in Chemical Formula 1,
Y$^1$ to Y$^4$ are independently CR$^x$R$^y$ or NR$^z$ (wherein R$^x$, R$^y$, and R$^z$ are hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ are independently hydrogen or a substituted or unsubstituted C1 to C10 alkyl group), or a combination thereof, provided that at least one of Y$^1$ to Y$^4$ is NR$^z$, and
Y$^5$ and Y$^6$ are independently CR$^x$R$^y$ or NR$^z$ (wherein R$^x$, R$^y$ and R$^z$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ are independently hydrogen or a substituted or unsubstituted C1 to C10 alkyl group).

10. The compound of claim 1, wherein the compound has a maximum absorption wavelength ($\lambda_{max}$) in a wavelength range of about 500 nm to about 600 nm in a thin film state.

11. The compound of claim 1, wherein the compound exhibits a light absorption curve having a full width at half maximum (FWHM) of about 50 nm to about 150 nm, in a thin film state.

12. The compound of claim 1, wherein a difference between a melting point of the compound and a temperature at which 10 wt % of an initial weight is lost (deposition temperature) is greater than or equal to about 10° C.

13. A photoelectric device, comprising
a first electrode and a second electrode facing each other, and
an active layer between the first electrode and the second electrode
wherein the active layer comprises the compound of claim 1.

14. An image sensor comprising:
the photoelectric device of claim 13.

15. The image sensor of claim 14, wherein
the image sensor comprises a semiconductor substrate,
the photoelectric device is on the semiconductor substrate and selectively sensing light in a green wavelength region, and
the semiconductor substrate is integrated with a plurality of first photo-sensing devices sensing light in a blue wavelength region and a plurality of second photo-sensing devices sensing light in a red wavelength region.

16. The image sensor of claim 15, further comprising:
a color filter layer comprising a blue filter selectively transmitting light in a blue wavelength region and a red filter selectively transmitting light in a red wavelength region.

17. The image sensor of claim 15, wherein the first photo-sensing device and the second photo-sensing device are stacked in a vertical direction in the semiconductor substrate.

18. The image sensor of claim 14, wherein
the photoelectric device is a green photoelectric device that is an organic photoelectric device,
the image sensor comprises a blue photoelectric device selectively absorbing light in a blue wavelength region and a red photoelectric device selectively absorbing light in a red wavelength region, and
the green photoelectric device, the blue photoelectric device, and the red photoelectric device are stacked.

19. An electronic device comprising:
the image sensor of claim 14.

* * * * *